US012702732B2

(12) United States Patent
Yusa et al.

(10) Patent No.: US 12,702,732 B2
(45) **Date of Patent: *Aug. 11, 2026**

(54) METAL MATERIAL HAVING BIOLOGICAL PROPERTIES

(71) Applicant: KOMATSUSEIKI KOSAKUSHO CO., LTD., Suwa-City (JP)

(72) Inventors: Fumie Yusa, Ikoma-City (JP); Thomas J. Webster, Barrington, RI (US); Takafumi Komatsu, Suwa-City (JP)

(73) Assignee: KOMATSUSEIKI KOSAKUSHO CO., LTD, Suwa (JP)

( * ) Notice: Subject to any disclaimer, the term of this patent is extended or adjusted under 35 U.S.C. 154(b) by 989 days.

This patent is subject to a terminal disclaimer.

(21) Appl. No.: 17/273,807

(22) PCT Filed: Sep. 27, 2019

(86) PCT No.: PCT/IB2019/001041
§ 371 (c)(1),
(2) Date: Mar. 5, 2021

(87) PCT Pub. No.: WO2020/065397
PCT Pub. Date: Apr. 2, 2020

(65) Prior Publication Data

US 2022/0226548 A1 Jul. 21, 2022

Related U.S. Application Data

(60) Provisional application No. 62/822,134, filed on Mar. 22, 2019.

(30) Foreign Application Priority Data

Sep. 28, 2018 (JP) ................................ 2018-183688

(51) Int. Cl.
*A61L 31/16* (2006.01)
*A61L 31/02* (2006.01)
*C22C 38/18* (2006.01)

(52) U.S. Cl.
CPC ............ *A61L 31/16* (2013.01); *A61L 31/022* (2013.01); *A61L 2300/404* (2013.01);
(Continued)

(58) Field of Classification Search
CPC .. A61L 31/16; A61L 31/022; A61L 2300/404; A61L 2300/412;
(Continued)

(56) References Cited

U.S. PATENT DOCUMENTS 6,391,253 B1 * 5/2002 Tochihara ............... C22C 38/22 148/609
2003/0083731 A1 * 5/2003 Kramer .................. A61L 29/02 623/1.15

(Continued)

FOREIGN PATENT DOCUMENTS

CN 108531817 A 9/2018
EP 992599 A1 4/2000

(Continued)

OTHER PUBLICATIONS

Bin Yu, et al., "Surface Nanocrystallization for Bacterial Control," Langmuir, 2010, 26 (13), pp. 10930-10934 (hereafter, "Yu"). (Year: 2010).*

(Continued)

*Primary Examiner* — John A Hevey
(74) *Attorney, Agent, or Firm* — WHDA, LLP

(57) ABSTRACT

Aspects of the invention relate to a metal material and product made from the metal material having biological properties, such as antibiotic properties.

14 Claims, 25 Drawing Sheets

(52) U.S. Cl.
CPC ... *A61L 2300/412* (2013.01); *A61L 2300/424* (2013.01); *C22C 38/18* (2013.01); *C22C 2200/04* (2013.01)

(58) Field of Classification Search
CPC .. A61L 2300/424; A61L 27/042; A61L 27/50; A61L 27/54; A61L 29/02; A61L 29/14; A61L 31/14; A61L 27/06; A61L 29/16; C22C 38/00; C22C 38/18; C22C 2200/04; A61B 2017/00889; A61M 25/0017; A61M 2025/0056; C21D 6/004; C21D 8/0273; C21D 9/46; C21D 2201/03; C21D 8/0205
See application file for complete search history.

(56) References Cited

U.S. PATENT DOCUMENTS

2012/0141562 A1 6/2012 Achneck et al.
2014/0342954 A1* 11/2014 Ingber .................... A61L 29/08 210/502.1
2016/0216254 A1* 7/2016 Morishita ........ G01N 33/54366
2021/0298320 A1* 9/2021 Komatsu ................. C12N 1/38
2022/0010417 A1* 1/2022 Yusa ...................... C22C 38/02
2022/0226548 A1 7/2022 Yusa et al.

FOREIGN PATENT DOCUMENTS

JP 2000-096165 A 4/2000
JP 2018-100449 A 6/2018

OTHER PUBLICATIONS

Jang et al., "Inhibition of Bacterial Adhesion on Nanotextured Stainless Steel 316L by Electrochemical Etching," ACS Biomater. Sci. Eng. 2018, 4, pp. 90-97. (Published Dec. 12, 2017) (Year: 2017).*
Sharma et al., "Subnanometric Roughness Affects the Deposition and Mobile Adhesion of *Escherichia coli* on Silanized Glass Surfaces," Langmuir, 2016, 32, pp. 5422-5433 (Year: 2016).*
Frost et al., "Sub-nanometer Smoothing of Diamond-turned Metal Surfaces using Ion Beams," Towards Synthesis of Micro-/Nano-systems, The 11th International Conference on Precision Engineering, Aub. 16-18, 2006, JSPE Pub. Series No. 5, pp. 239-242 (Year: 2016).*
Office Action dated Oct. 18, 2022, issued in JP application no. 2021-529351, with English translation (counterpart to U.S. Appl. No. 17/289,960) (8 pages).
Office Action dated Oct. 27, 2022, issued in counterpart JP application No. 2021-510672, with English translation. (12 pages).
Examination Report dated Oct. 10, 2022, issued in counterpart AU application No. 2019346107. (6 pages).
Examination Report dated Oct. 10, 2022, issued in AU application No. 2020245240 (counterpart to U.S. Appl. No. 17/289,960). (5 pages).
Song et al., "Overview of processing, microstructure and mechanical properties of ultrafine grained bcc steels", Materials Science & Engineering A, 2006, vol. 441, No. 1-2, pp. 1-17, cited in both IN Office Actions dated Oct. 10, 2022. (17 pages).
Supplementary European Search Report dated Aug. 29, 2022, issued in counterpart EP application No. 20 77 9234.2 (10 pages).
Sreekumari, Kurissery R et al., "Bacterial attachment to stainless steel welds: Significance of substratum microstructure", Biofouling: the Journal of Bioadhesion and Biofilm research, vol. 17, No. 4, Dec. 1, 2002 (Dec. 1, 2001), pp. 303-316, XP055855134, GN ISSN: 0892-7014, DOI: 10.1080/08927010109378490 Retrieved from the Internet: <URL:https://www.tandfonline.com/doi/pdf/10.1080/08927010109378490?needAccess=true *the> whole document*.
Decision of Dismissal of Amendment dated May 18, 2023, issued in counterpart JP Application No. 2021-510672, with English translation. (9 pages).
International Search Report dated Feb. 25, 2020, issued in counterpart application No. PCT/IB2019/001041 (3 pages).
Bassous et al., "3-D printed Ti-6A1-4V scaffolds for supporting osteoblast and restricting bacterial functions without using drugs: Predictive equations and experiments", Acta Biomaterialia, 2019, 96, pp. 662-673 (12 pages).
Liu et al., "Understanding the Role of Polymer Surface Nanoscale Topography on Inhibiting Bacteria Adhesion and Growth", ACS Biomaterials Science and Engineering, 2016, 2 (1), pp. 122-130, (9 pages).
Günay-Bulutsuz et al., "Biological responses of ultrafine grained pure titanium and their sand blasted surfaces", Materials Science & Engineering C, May 18, 2018, vol. 91, pp. 382-388, (7 pages).
Yu et al., "Surface Nanocrystallization for Bacterial Control", Langmuir, 2010, vol. 26, pp. 10930-10934, (5 bages).
Bagherifard et al., "The influence of nanostructured features on bacterial adhesion and bone cell functions on severely shot peened 316L stainless steel", Biomaterials, Sep. 12, 2015, vol. 73, pp. 185-197, (13 bages).
Tufan et al., "Efficient fabrication of ultrafine-grained 316L stainless steel surfaces for orthopaedic applications", Materials Science and Technology, Aug. 25, 2019, vol. 35, pp. 1891-1897, (7 pages).
Gong et al., "On the mechanical behavior of austenitic stainless steel with nano/ultrafine grains and comparison with micrometer austenitic grains counterpart and their biological functions", Journal of the Mechanical Behavior of Biomedical Materials, Sep. 14, 2019, vol. 101, 103433, (7 pages).
Office Action dated May 13, 2022, issued in counterpart JP application No. 2021-529351, with English translation (counterpart to U.S. Appl. No. 17/289,960). (11 pages).
Extended (Supplementary) European Search Report dated Apr. 8, 2022, issued in counterpart EP application No. 19867194.3. (10 pages).
Sreekumari et al., "Bacterial attachment to stainless steel welds: Significance of substratum microstructure", BIOFOULING: The Journal of Bioadhesion and Biofilm Research, 2001, vol. 17, No. 4, pp. 303-316, cited in EP Extended European Search Report dated Apr. 8, 2022. (15 pages).
Truong et al., "Effect of ultrafine-grained titanium surfaces on adhesion of bacteria", Applied Microbiology and Biotechnology, 2009, vol. 83, No. 5, pp. 925-937, cited in EP Extended European Search Report dated Apr. 8, 2022. (13 pages).
Office Action dated Feb. 22, 2022, issued in counterpart JP Application No. 2021-510672, with English Translation. (12 pages).
Office Action dated Mar. 8, 2022, issued in counterpart AU Application No. 2019346107. (3 pages).
Office Action dated Mar. 10, 2022, issued in AU Application No. 2020245240. (Issued in counterpart U.S. Appl. No. 17/289,960) (4 pages).
Notification Concerning Transmittal of International Preliminary Report on Patentability (Forms PCT/IB/326). Issued in counterpart International Application No. PCT/IB2019/001041 mailed Apr. 8, 2021 with Forms PCT/IB/373 and PCT/ISA/237. (8 pages).
Non-Final or Final Office Action dated May 22, 2024, issued in U.S. Appl. No. 17/289,960 (49 pages).
Murray et al., Evaluation of Bactericidal and anti-biofilm properties of a novel surface-active organosilane biocide against healthcare associated pathogens and Pseudomonas aeruginosa biofilm, PLOS one, Aug. 7, 2017 (Year: 2017).
Office Action dated Dec. 23, 2025, issued in counterpart CN Application No. 202080018535.5, with English translation and brief explanation. (35 pages).
Deng, B. et al., Mechanical Properties of As-Cast 304L Austenitic Stainless Steel During Equal Channel Angular Pressing, Journal of Iron and Steel Research, vol. 20, No. 3, p. 40-44, 2008, with English Abstract. (5 pages).

(56) References Cited

OTHER PUBLICATIONS

Office Action dated May 16, 2026, issued in counterpart CN Application No. 202080018535.5, with English translation and a brief explanation. (20 pages).

* cited by examiner

UFGSS size:

y = 8E+07x - 1E+07

$R^2$ = 0.6989

CG samples:

y = 169680x + 126660

$R^2$ = 0.9582

Optimal grain size (CFU/ml=0):

- 0.74 µm and 0.125 µm

UFGSS size:

y = 3E+06x – 497554

$R^2$ = 0.6968

CG samples:

y = 6598.3x - 28273

$R^2$ = 0.9866

Optimal grain size: 4.28 µm and 0.16 µm

UFGSS size:

y = 4E+07x - 6E+06

$R^2 = 0.9914$

CG samples:

y = 83210x + 1E+06

$R^2 = 0.123$

UFGSS size:

y = -3E+07x + 1E+07

$R^2 = 0.0735$

CG samples:

y = -525563x + 1E+07

$R^2 = 0.9737$

Optimal grain size: 19.02 µm and 0.33 µm

UFGSS size:

y = 13.744x - 0.5786

$R^2$ = 0.086

CG samples:

y = -0.0886x + 2.278

$R^2$ = 0.7873

Optimal grain size (CFU/ml=0): 25.71 μm and 0.04 μm

UFGSS size:

y = 8.2923x - 1.5736

$R^2$ = 0.7587

CG samples:

y = 0.0162x + 0.2547

$R^2$ = 0.4581

Optimal grain size:

-15.72 µm and 0.19 µm

UFGSS size:

y = 3.6085x + 0.243

$R^2 = 0.3544$

CG samples:

y = -0.2006x + 3.7718

$R^2 = 0.4803$

Optimal grain size: 18.80 µm and -0.07 µm

UFGSS size:

y = -51.965x + 14.374

$R^2$ = 0.526

CG samples:

y = -0.8585x + 14.133

$R^2$ = 0.8462

Optimal grain size: 16.46 µm and 0.28 µm

UFGSS samples:

$y = -33.987x + 10.3$ $R^2 = 0.461$

CG samples:

$y = -0.1309x + 4.0134$ $R^2 = 0.9355$

Optimal grain size (CFU/ml=0): 30.66 µm and 0.30 µm

UFGSS samples:

y = -7.9106x + 2.3144

$R^2 = 0.4623$

CG samples:

y = 0.0636x - 0.6

$R^2 = 0.8129$

Optimal grain size: 9.43 µm and 0.29 µm

| UFGSS size: | CG samples: |
|---|---|
| y = -1.3403x + 2.1296 | y = -0.1418x + 3.9434 |
| $R^2$ = 0.0024 | $R^2$ = 0.2659 |

Optimal grain size: 27.81 µm and 1.59 µm

UFGSS size:

$y = -4.4798x + 3.1221$ $R^2 = 0.0072$

CG samples:

$y = -0.1131x + 3.6461$ $R^2 = 0.3171$

Optimal grain size: 32.23 µm and 0.70 µm

FIG. 7C

| | | viability (%) |
|---|---|---|
| **Grain size (μm)** | **Sample** | **Day 3** |
| **0.23** | UFGSS SUS 304 8.04mm$^2$ | 92.88 |
| **15** | CG SUS 304 8.04mm$^2$ | 88.67 |
| **0.22** | UFGSS SUS 304 16.21mm$^2$ | 102.55 |
| **12** | CG SUS 304 16.21mm$^2$ | 92.89 |
| **0.27** | UFGSS SUS 304 32.92mm$^2$ | 108.56 |
| **21.5** | CG SUS 304 32.92mm$^2$ | 96.81 |

FIG. 8C

| | | viability (%) |
|---|---|---|
| **Grain size (μm)** | **Sample** | **Day 3** |
| **0.18** | UFGSS SUS 316 8.04mm$^2$ | 95.09 |
| **7.1** | CG SUS 316 8.04mm$^2$ | 91.80 |
| **0.22** | UFGSS SUS 316 16.21mm$^2$ | 89.53 |
| **10.7** | CG SUS 316 16.21mm$^2$ | 94.52 |
| **0.25** | UFGSS SUS 316 32.92mm$^2$ | 91.503 |
| **16.5** | CG SUS 316 32.92mm$^2$ | 101.10 |

Control sample: $1.99 \cdot 10^5$ cells; optimal grain size ($y \geq 1.99 \cdot 10^5$ cells)

Optimal grain size:

304 CG ≥ 9.49 μm or 22.71 μm

304 UFGSS ≥ 0.23 μm

Control sample: $1.99 \cdot 10^5$ cells; optimal grain size ($y \geq 1.99 \cdot 10^5$ cells)

Optimal grain size:

316 CG ≥ 15.88 μm

316 UFGSS ≥ 0.07 μm

*p<0.05 respect control 1, on day 5

**p<0.05 respect control 2, on day 5

METAL MATERIAL HAVING BIOLOGICAL PROPERTIES

RELATED APPLICATIONS

This application claims priority to U.S. Provisional Application Ser. No. 62/822,134, filed Mar. 22, 2019, and to Japanese Patent Application No. 2018-183688, filed Sep. 28, 2018, the disclosure of each of which are hereby incorporated herein by reference to their entireties.

FIELD

Aspects of the present disclosure relate to a metal material and metallic devices having biological properties.

BACKGROUND

Reports have shown that about 400,000 vascular catheter-related bacteremias and fungemias occur annually in the United States. Such infections can be life-threatening, and are generally difficult to treat. Bactericidal action to reduce or prevent colonization are typically by coating the device with antibiotics.

Alternatively, it is desirable for implantable devices, to increase or decrease adhesion and/or growth of eukaryotic cells.

SUMMARY

"Aspects of the disclosure relate to metal materials and devices having a grain size that provide a surface energy promoting antibacterial action, improvement in eukaryotic cell growth or combination thereof."

Aspects of the disclosure relate to metal materials comprising a crystal grain having an average crystal grain size from 40 nm to 30 μm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells."

In some embodiments, the metal material inhibits adsorption or growth of microorganisms on the metal material by at least 50%. In some embodiments, the microorganism is a gram+bacterium. In some embodiments, the microorganism is a gram−bacterium. In some embodiments, the microorganism is one of *Staphylococcus aureus, Staphylococcus epidermidis*, Methicillin-resistant *Staphylococcus aureus* (MRSA), *E. coli, Pseudomonas aeruginosa.*

In some embodiments, the metal material decreases inflammatory cell adsorption or growth, decrease bacterial adsorption or growth, increase osteoblast adsorption or growth, increase endothelial cell adsorption or growth or combinations thereof.

In some embodiments, the metal material has an average crystal grain size for substantially inhibiting adsorption or growth of the microorganism which is determined from a response profile which is a result obtained by cultivating the microorganism on a metal material having crystal grains with different average crystal grain sizes and plotting a number of the microorganism after the cultivation with respect to the average crystal grain size."

In some embodiments, the crystal grain has an average crystal grain size from 200 nm or more to 10 μm or less. In some embodiments, the crystal grain has an average crystal grain size from 600 nm or more to 10 μm or less."

In some embodiments, the crystal grain has an average crystal grain size from 1 μm or more to 10 μm or less. In some embodiments, the crystal grain has an average crystal grain size from 4 μm or more to 10 μm or less.

In some embodiments, the material is polished has a surface roughness at the nanoscale from 0.1 nm to 100 μm."

In some embodiments, the metal material can be stainless steel. In some embodiments, the metal material can be type 316 stainless steel.

In some embodiments, the metal material is a wire or a rod. In some embodiments, the average crystal grain size is from 200 nm or more to 10 μm or less. In some embodiments, the average crystal grain size is from 600 nm to 10 μm.

Some aspects of the disclosure relate to a medical device made from the metal material described herein."

Some aspects of the disclosure relate a foil made from the material metal described herein.

Some aspects of the disclosure relate to an instrument made from the material metal material described herein.

Some aspects of the disclosure relate to a metal wire comprising a crystal grain having an average crystal grain size from 200 nm to 10 μm, wherein the metal wire has antibiotic properties. In some embodiments, the average crystal grain size is from 600 nm to 10 μm.

Some aspects of the disclosure relate to comprising a metallic medical device comprising a crystal grain having an average crystal grain size from 200 nm to 10 μm, wherein the medical device has antibiotic properties. In some embodiments, the average crystal grain size is from 600 nm to 10 μm.

In some embodiments, the metallic medical device inhibits adsorption or growth of microorganisms on the metallic medical device by at least 50%.

BRIEF DESCRIPTION OF THE DRAWINGS

FIGS. 7A-7C show the percent viability of the human dermal fibroblast when grown on type 304 stainless steel metal samples with different grain sizes according to some embodiments.

FIGS. 8A-8C show the percent viability of the human dermal fibroblast when grown on type 316 stainless steel metal samples with different grain sizes according to some embodiments.

DETAILED DESCRIPTION

Figure 1A:
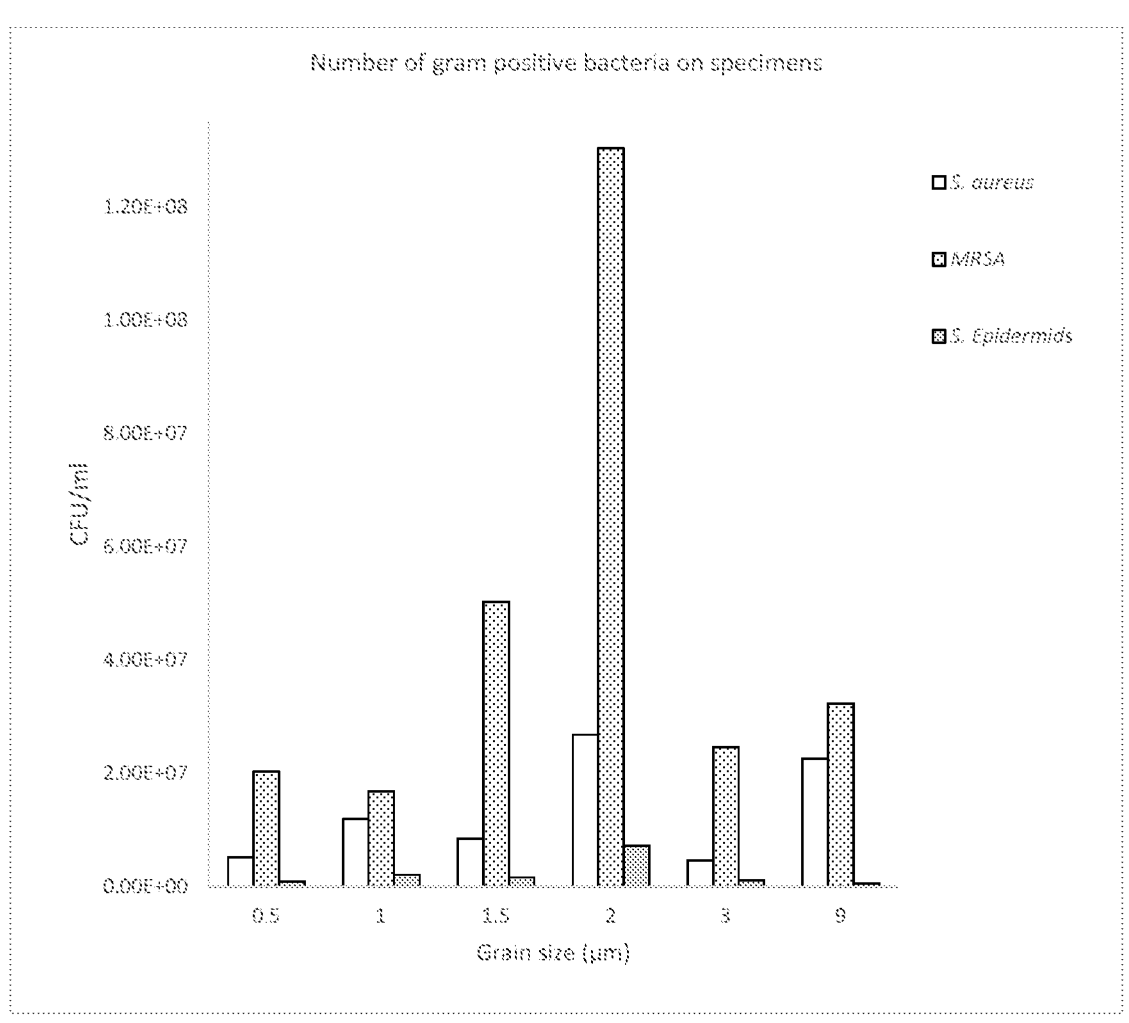
FIG. 1A is an example of a response profile obtained by plotting a response amount (CFU/ml) of gram positive bacteria (*S. aureus*, Methicillin-resistant *Staphylococcus aureus, S. epidermidis*) with respect to an average crystal grain size of a crystal grain according to some embodiments.

Metal materials having refined crystal grains are superior in characteristics such as strength, toughness, and corrosion resistance as compared with metal materials having coarse crystal grains. Accordingly, the metal materials are widely used in various industrial applications such as steel plates and medical devices.

Some aspects of the disclosure relate to a metal that is processed so as to form a recrystallized metal material having an average crystal grain size ranging from 0.01 to 20 μm, 0.04 to 20 μm, 0.05 to 30 μm, 0.1 μm to 30 μm, from 0.5 μm to 30 μm, from 1 μm to 30 μm, from 2 μm to 30 μm, from 3 μm to 30 μm, from 4 μm to 30 μm, from 5 μm to 30 μm, from 6 μm to 30 μm, from 7 μm to 30 μm, from 8 μm to 30 μm, from 9 μm to 30 μm, from 10 μm to 30 μm, from 15 μm to 30 μm, from 20 μm to 30 μm, from 15 μm to 30 μm, from 16 μm to 30 μm, from 17 μm to 30 μm, from 18 μm to 30 μm, from 19 μm to 30 μm 0.1 μm to 20 μm, from 0.5 μm to 20 μm, from 1 μm to 20 μm, from 2 μm to 20 μm, from 3 μm to 20 μm, from 4 μm to 20 μm, from 5 μm to 20 μm, from 6 μm to 20 μm, from 7 μm to 20 μm, from 8 μm to 20 μm, from 9 μm to 20 μm, from 10 μm to 20 μm, from 11 μm to 20 μm, from 12 μm to 20 μm, from 13 μm to 20 μm, from 14 μm to 20 μm, from 15 μm to 20 μm, from 16 μm to 20 μm, from 17 μm to 20 μm, from 18 μm to 20 μm, from 19 μm to 20 μm, 0.1 μm to 10 μm, from 0.5 μm to 10 μm, from 1 μm to 10 μm, from 2 μm to 10 μm, from 3 μm to 10 μm, from 4 μm to 10 μm, from 5 μm to 10 μm, from 6 μm to 10 μm, from 7 μm to 10 μm, from 8 μm to 10 μm, from 9 μm to 10 μm, from 1 μm to 2 μm, from 2 μm to 3 μm, from 3 μm to 4 μm, from 4 μm to 5 μm, from 5 μm to 6 μm, from 6 μm to 7 μm, from 7 μm to 8 μm, from 8 μm to 9 μm, about 0.01 μm, about 0.02 μm, about 0.03 μm, about 0.04 μm, about 0.05 μm, about 0.06 μm, about 0.07 μm, about 0.08 μm, about 0.09 μm, about 0.1 μm, about 0.2 μm, about 0.3 μm, about 0.4 μm, about 0.5 μm, about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 25 μm, about 26 μm, about 27 μm, about 28 μm, about 29 μm, about 30 μm or higher or any range therebetween.

It should be appreciated that the metal material can have a homogenous average crystal grain size. In some embodiments, the metal comprises an average grain size of about 1 μm±20%, about 2 μm±20%, about 3 μm±20%, about 4 μm±20%, about 5 μm±20%, about 6 μm±20%, about 7 μm±20%, about 8 μm±20%, about 9 μm±20%, about 10 μm±20% or any range therebetween. In some embodiments, the metal comprises an average grain size of about 10 μm±40%, about 11 μm±40%, about 12 μm±40%, about 13 μm±40%, about 14 μm±40%, about 15 μm±40%, about 16 μm±40%, about 17 μm±40%, about 18 μm±40%, about 19 μm±40%, about 20 μm±40%, about 21 μm±40%, about 22 μm±40%, about 23 μm±40%, about 25 μm±40%, about 26 μm±40%, about 27 μm±40%, about 28 μm±40%, about 29 μm±40%, about 30 μm±40% or any range therebetween.

In some aspects, the metal is 304 stainless steel metal having an average crystal grain size ranging from about 0.22 μm to about 22 μm, for example 0.22 to 21.50 μm. In some embodiments, the 304 stainless steel metal has a composition described at Table 6.

In some aspects, the metal is 316 stainless steel metal having an average crystal grain size ranging from about 0.16 μm to about 17 μm, for example, 0.16 μm to 16.50 μm. In some embodiments, the 316 stainless steel metal has a composition described at Table 4.

In some aspects, the metal is titanium or titanium alloy having a crystal grain size ranging from about 0.8 μm to about 9 μm, for example 0.8 to 8.80 μm. In some embodiments, the titanium alloy is β-titanium (Ti-15V-3Cr-3Sn-3Al), Ti-6Al-4V, or combinations thereof.

In some embodiments, the metal material can be processed to tailor the crystal grain size so as to control cell adhesion, cell growth or combination thereof. In some embodiments, the metal material or device can have an average grain size to inhibit adhesion, growth or combination thereof of bacteria. In some embodiments, the metal material or device can have an average grain size to increase the adhesion, growth or combinations thereof of predetermined eukaryotic cells. In some embodiments, the metal material or device can have an average grain size to inhibit adhesion, growth or combination thereof of predetermined eukaryotic cells. In some embodiments, the metal material or device can have (i) an average grain size to inhibit adhesion, growth or combination thereof of bacteria, (ii) an average grain size to promote adhesion, growth or combination thereof of predetermined eukaryotic cells and (iii) an average grain size to inhibit adhesion, growth or combination thereof of predetermined eukaryotic cells.

Metal Material Having Antibiotic Property

The term "antibiotic property" as used herein refer to property of preventing or reducing the growth or reproduction or adhesion of a microorganism (such as bacterial and fungal organisms), or of killing a microorganism.

The term "bacterial and fungal organisms" as used in the present invention means all genus and species of bacteria and fungi, including but not limited to all spherical, rod-shaped, and spiral bacteria. Non-limiting examples of bacteria include staphylococci (e.g., *Staphylococcus epidermidis, Staphylococcus aureus*), *Enterococcus faecalis, Pseudomonas aeruginosa, Escherichia coli, Clostridioides difficile* among other gram-positive bacteria and gram-negative bacilli. Non-limiting examples of fungal organisms include *Candida albicans, Candida krusei, Candida parapsilosis, Candida* spp, *Candida pseudotropicalis, Candida glabrata, Candida lusitaniae*, and *Candida tropicalis.*

In some embodiments, the bacteria are gram positive bacteria including, but not limited to, *Staphylococcus aureus, Staphylococcus epidermidis*, Methicillin-resistant *Staphylococcus aureus* (MRSA), or the like. In some embodiments, the bacteria are gram negative bacteria including, but not limited to, *Pseudomonas aeruginosa, E. coli, Klebsiella pneumoniae, Legionella pneumophila, Proteus mirabilis, Enterobacter cloacae, Serratia marcescens, Helicobacter pylori, Salmonella enteritidis*, and *Salmonella typhi.*

Aspects of the invention provide for a metal material and methods for providing efficacious broad spectrum anti-infective protection to a metal material, including but not limited to, protection against resistant staphylococci, MDR gram negative bacteria (such as MDR *Pseudomonas aeruginosa*).

Aspects of the invention provide metal material having an improved antibiotic property. In some embodiments, the metal material can be used in medical devices. In some embodiments, the metal material can be used in surgical instruments, vascular stent, endoscopic instruments, catheter parts, guide wire, kirschner wires (K-wire), pins, screw, etc. or implantable medical devices. In some embodiments, the metal material can be used in surgical instruments. In some embodiments, the metal material can be used in biosensors. In some embodiments, the metal material can be used in kitchenware. In some embodiments, the metal material can be used in experimental tools. In some embodiments, the metal material can be used in a kirschner wire.

Non-limiting examples of medical devices include vascular catheters, such as peripherally insertable central venous catheters, dialysis catheters, long term tunneled central venous catheters, peripheral venous catheters, single-lumen and multiple-lumen short-term central venous catheters, arterial catheters, pulmonary artery Swan-Ganz catheters, and the like, urinary catheters, other long term urinary devices, tissue bonding urinary devices, renal stents, penile prostheses, vascular grafts, vascular access ports, wound drain tubes, hydrocephalus shunts, ventricular drainage catheters, neurologic and epidural catheters, neurostimulators, peritoneal dialysis catheters, pacemaker capsules, artificial urinary sphincters, small or temporary joint replacements, dilators, heart valves, orthopedic prosthesis, spinal hardware, surgical site repair mesh (e.g., hernia mesh), endotracheal tubes, biliary stents, gastrointestinal tubes, colorectal tract implants, male and female reproductive implants, cosmetic or reconstructive implants, stethoscope drums, orthopedic implants (e.g., joint (knee, hip, elbow, shoulder, ankle), prostheses, external fixation pins, intramedullary rods and nails, spine implants), cardiac pacemakers, defibrillators, electronic device leads, adaptors, lead extensions, implantable infusion devices, implantable pulse generators, implantable physiological monitoring devices, devices for locating an implantable pulse generator or implantable infusion device under the skin, and devices (e.g. refill needles and port access cannulae) for refilling an implantable infusion device or other medical and indwelling devices that may be subject to microbial infestation.

In some embodiments, the device are stainless steel devices and can be used for, but not limited to, high speed surgical drill, vertebroplasty and kyphoplasty devices, minimally invasive surgical instruments and endoscopy devices, orthopedic implants, and surgical instruments.

In some embodiments, the device are titanium devices and can be used for but not limited to, orthopedic implants, dental implants, spinal implants, minimally invasive surgical instruments and endoscopy devices, and surgical instruments.

In some embodiments, the antibiotic property of the metal material is achieved without the addition of an antibiotic agent in or onto the metal material.

In some embodiment, the metal material inhibits adhesion of bacterial cells by 100%, 95%, 90%, 80%, 70%, 60%, 50%, 40%, 30%, 20%, 10%, or by at least by 5% or any value or range therebetween.

Metal Material Promoting Cell Adhesion or Inhibiting Cell Adhesion

In some embodiments, it is desirable to increase the adhesion of cells onto a metallic material, such as metallic implant. In other embodiments, it is desirable the decrease or inhibit the adhesion of cells onto a metallic material, such as a metallic implant. For example, it may be desirable to increase the adhesion of osteoblast on the surface of the orthopedic implant. In other examples it may be desirable to increase the adhesion of endothelial cells on the surface of the vascular stents or implant and to inhibit the adhesion of fibroblast onto the vascular stents or implant.

In some embodiments, the metal material described herein can improve the adhesion and/or growth of eukaryotic cells such as osteoblasts, fibroblasts, chondrocytes, endothelial cells, keratinocytes, smooth muscle cells, urothelial cells, osteoclasts, osteocytes, stem cells, mesenchymal stem cells, induced pluripotent stem cells, neurons, astrocytes, Schwann cells, meningeal cells, epithelial cells, etc. . . . .

In some embodiments, the metal material described herein has a surface energy that promotes cell adhesion and/or growth of some eukaryotic cells. In some embodiment, the metal material increases cell adhesion and/or growth by at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or any value or range therebetween.

Yet in some embodiments, the metal material described herein has a surface energy that inhibits cell adhesion and/or growth of other eukaryotic cells. In some embodiment, the metal material decreases cell adhesion and/or growth at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or any value or range therebetween.

In some embodiments, the metal material described herein has antibiotic properties and improve the adhesion and/or growth of eukaryotic cells such as osteoblasts, fibroblasts, endothelial cells, chondrocytes, endothelial cells, keratinocytes, smooth muscle cells, urothelial cells, osteoclasts, osteocytes, stem cells, mesenchymal stem cells, induced pluripotent stem cells, neurons, astrocytes, Schwann cells, meningeal cells, epithelial cells, etc. . . . .

In some embodiments, the metal material described herein has antibiotic properties and inhibits the adhesion and/or growth of eukaryotic cells such as immune cells.

The metal material and the use of the metal material to (i) reduce or inhibit bacterial adhesion and/or growth, (ii) improve or to the adhesion and/or growth of eukaryotic cells such as osteoblasts, fibroblasts, etc, (iii) reduce or inhibit adhesion and/or growth of immune cells, or (iv) (i) reduce or inhibit bacterial adhesion and/or growth, (ii) improve adhesion and/or growth of eukaryotic cells such as osteoblasts, fibroblasts etc, (iii) reduce or inhibit adhesion and/or growth of immune cells or any combinations of (i), (ii) and (iii) is described herein below.

Uses of Metal Material

In some embodiments, the metal material can be used in medical devices. For example, the metal material can be used in vascular stent, endoscopic instruments, surgical instruments, catheter parts, guide wire, kirschner wires, pins, screw, etc. or implantable medical devices.

In some embodiments, the metal material can be used in biosensors. In some embodiments, the metal material can be used in kitchenware. In some embodiments, the metal material can be used in experimental tools.

Non-limiting examples of medical devices include vascular catheters, such as peripherally insertable central venous catheters, dialysis catheters, long term tunneled central venous catheters, peripheral venous catheters, single-lumen and multiple-lumen short-term central venous catheters, arterial catheters, pulmonary artery Swan-Ganz catheters, and the like, urinary catheters, other long term urinary devices, tissue bonding urinary devices, renal stents, penile prostheses, vascular grafts, vascular access ports, wound drain tubes, hydrocephalus shunts, ventricular drainage catheters, neurologic and epidural catheters, neurostimulators, peritoneal dialysis catheters, pacemaker capsules, artificial urinary sphincters, small or temporary joint replacements, dilators, heart valves, orthopedic prosthesis, spinal hardware, surgical site repair mesh (e.g., hernia mesh), endotracheal tubes, biliary stents, gastrointestinal tubes, colorectal tract implants, male and female reproductive implants, cosmetic or reconstructive implants, stethoscope drums, orthopedic implants (e.g., joint (knee, hip, elbow, shoulder, ankle), prostheses, external fixation pins, intramedullary rods and nails, spine implants), cardiac pacemakers, defibrillators, electronic device leads, adaptors, lead extensions, implantable infusion devices, implantable pulse generators, implantable physiological monitoring devices, devices for locating an implantable pulse generator or implantable infusion device under the skin, and devices (e.g. refill needles and port access cannulae) for refilling an implantable infusion device or other medical and indwelling devices that may be subject to microbial infestation.

Some embodiments relate to surgical instruments.

In some embodiments, the device is a K-wire.

In some embodiments, the device is an implantable orthopedic implant.

In some embodiments, the device is a vascular stent.

Composition

Known metal materials for medical device application may be used, and examples of the metal materials include iron, stainless steel, aluminum, silver, copper, titanium, tin, nickel, zinc, chromium, and alloys of these metal materials. Among them, stainless steel is preferable in view of easy controllability of the crystal grain size of the crystal grain, versatility, ready availability, processability, and low toxicity. The stainless steel is not particularly limited, and may be any of martensitic stainless steel, ferritic stainless steel, austenitic stainless steel, austenite/ferrite stainless steel, and precipitation hardening stainless steel.

In some embodiments, the metal material is stainless steel or a stainless-steel alloy. For example, the metal material can be type 304 stainless steel or type 316 stainless steel. The type 316 stainless steel differs from the type 304 by the presence of molybdenum. In some embodiments, the stainless steel material can comprise from 6 to 22% nickel. In some embodiments, the stainless steel material can also contain other alloying elements, such as chromium (16 to 26%) for corrosion resistance. In some embodiments, the stainless steel can comprise manganese and molybdenum. In some embodiments, the type 316 stainless steel can be used for medical devices.

In some embodiments, the metal material is titanium or titanium alloy. In some embodiments, the metal material is cobalt chromium. In some embodiments, the metal material is cobalt chromium molybdenum. In some embodiments, the metal material is nitinol.

Nanostructure

The metal material according to some embodiments is made of a fine crystal grain, which allows for the application to a wide range of devices.

The crystal grain forming the metal material according to some embodiments has an average crystal grain size for controlling the biological property of the metal material.

Aspects of the invention is based the phenomenon that biological property of the metal material depends on the average crystal grain size of the metal material.

In some aspects of the invention, the metal material described herein can have a crystal grain size, surface free energy and roughness that (i) reduces or inhibits bacterial adhesion and/or growth, (ii) improves or increases the adhesion and/or growth of eukaryotic cells such as osteoblasts, fibroblasts, etc, (iii) reduces or inhibits adhesion and/or growth of immune cells, or (iv) (i) reduce or inhibit bacterial adhesion and/or growth, (ii) improve adhesion and/or growth of eukaryotic cells such as osteoblasts, fibroblasts etc, (iii) reduce or inhibit adhesion and/or growth of immune cells or any combinations of (i), (ii) and (iii).

In some aspects of the invention, the metal material described herein can have a crystal grain size that is about the size of eukaryotic cells of a tissue under consideration and promote the adhesion and/or growth of the cells to the metal. In addition, the metal material described herein can have a surface free energy that promote the adhesion and/or growth of the cells to the metal. Furthermore, the metal material described herein can have a roughness that promote the adhesion and/or growth of the cells to the metal.

In some aspects of the invention, the metal material described herein can have a crystal grain size inhibits the adhesion and/or growth of the cells to the metal. In addition, the metal material described herein can have a surface free energy that promote the adhesion and/or growth of the cells to the metal. Furthermore, the metal material described herein can have a roughness that inhibits the adhesion and/or growth of the cells to the metal. In some embodiments, the cells are prokaryotic cells and/or eukaryotic cells.

Some aspects of the invention are based the phenomenon that antibiotic property of the metal material depends on the average crystal grain size of the metal material. In some embodiments, the metal material having a predetermined average crystal grain size ranging from about 0.01 to 30 μm. In some embodiments, the metal material having a predetermined average crystal grain size ranging from 0.01 to 500 μm. In some embodiments, the metal material provided herein can the growth of microorganisms and/or improve growth of osteoblasts and fibroblast. In some embodiments, the metal material provided herein can inhibit the growth, the immobilization or the growth and the immobilization (adsorption) of the microorganisms. In some embodiments, the metal material provided herein can inhibit the growth, the immobilization or the growth and the immobilization (adsorption) of the immune cells. In some embodiments, the metal material provided herein promotes the growth, the immobilization or the growth and the immobilization (adsorption) of predetermined eukaryotic cells.

Aspects of the invention relate to methods for inhibiting the growth, immobilization or growth and immobilization of microorganisms.

In some embodiments, the average crystal grain size for inhibiting the growth and/or immobilization of microorganisms can range from 0.01 to 20 μm, 0.01 to 30 μm, 0.04 to 20 μm, 0.05 to 30 μm, 0.1 μm to 30 μm, from 0.5 μm to 30 μm, from 1 μm to 30 μm, from 2 μm to 30 μm, from 3 μm to 30 μm, from 4 μm to 30 μm, from 5 μm to 30 μm, from 6 μm to 30 μm, from 7 μm to 30 μm, from 8 μm to 30 μm, from 9 μm to 30 μm, from 10 μm to 30 μm, from 15 μm to 30 μm, from 20 μm to 30 μm, from 15 μm to 30 μm, from 16 μm to 30 μm, from 17 μm to 30 μm, from 18 μm to 30 μm, from 19 μm to 30 μm 0.1 μm to 20 μm, from 0.5 μm to 20 μm, from 1 μm to 20 μm, from 2 μm to 20 μm, from 3 μm to 20 μm, from 4 μm to 20 μm, from 5 μm to 20 μm, from 6 μm to 20 μm, from 7 μm to 20 μm, from 8 μm to 20 μm, from 9 μm to 20 μm, from 10 μm to 20 μm, from 11 μm to 20 μm, from 12 μm to 20 μm, from 13 μm to 20 μm, from 14 μm to 20 μm, from 15 μm to 20 μm, from 16 μm to 20 μm, from 17 μm to 20 μm, from 18 μm to 20 μm, from 19 μm to 20 μm, 0.1 μm to 10 μm, from 0.5 μm to 10 μm, from 1 μm to 10 μm, from 2 μm to 10 μm, from 3 μm to 10 μm, from 4 μm to 10 μm, from 5 μm to 10 μm, from 6 μm to 10 μm, from 7 μm to 10 μm, from 8 μm to 10 μm, from 9 μm to 10 μm, from 1 μm to 2 μm, from 2 μm to 3 μm, from 3 μm to 4 μm, from 4 μm to 5 μm, from 5 μm to 6 μm, from 6 μm to 7 μm, from 7 μm to 8 μm, from 8 μm to 9 μm, about 0.01 μm, about 0.02 μm, about 0.03 μm, about 0.04 μm, about 0.05 μm, about 0.06 μm, about 0.07 μm, about 0.08 μm, about 0.09 μm, about 0.1 μm, about 0.2 μm, about 0.3 μm, about 0.4 μm, about 0.5 μm, about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 25 μm, about 26 μm, about 27 μm, about 28 μm, about 29 μm, about 30 μm or higher or any range therebetween.

In some embodiments, the average crystal grain size is greater than 0.5 μm but smaller than 10 μm. In some embodiments, the average crystal grain size is greater than 0.5 μm but smaller than 7 μm. In some embodiments, the average crystal grain size is greater than 1 μm but smaller than 7 μm. In some embodiments, the average crystal grain size is greater than 3 μm but smaller than 7 μm.

The grain boundaries can be measured by Electron backscatter diffraction (EBSD) and can show the different atoms low angles. The difference of angle can be greater 5 degrees. Each grain can be determined by an area surrounded by the grain-boundary lines. When the grain size is large, the shape is unique and random polygon. As the grain become smaller, the shape become smaller polygon, similar to a circle, a cubic, or rectangle. The short length for rectangle or diameter for circle is about the average grain size.

In some embodiments, the metal material has an average grain size of about 1 μm (+/−20%) or between 200 nm and 1 μm and inhibits the growth of gram positive and gram-negative bacteria. In some embodiments, the metal material has an average grain size of about 1 μm (+/−20%) or between 500 nm and 1 μm and inhibits the growth of gram positive and gram-negative bacteria.

During refining the crystal grain, the chemical composition of metal material does not change. Thus, any metal of different chemical composition can be used as long as it is a metal material having crystals or grains, such as for titanium, titanium-based materials, stainless steel, Co—Cr alloys, Co—Cr—Mo, nitinol, platinum, palladium, etc.

In some embodiments, the metal material, in addition to its antibiotic property has an improved tensile strength and hardness than conventional stainless steel.

As the method of adjusting the average crystal grain size of the crystal grain, a refinement method can be adopted. Examples of the method include a rolling process for the metal raw material before refinement, a shearing process, a compression process, a deforming process, and a combination of the processes. In this case, cooling or heating may be carried out, or refinement may be carried out in an atmosphere in the presence or absence of a specific gas (such as oxygen or nitrogen). Generally, the refinement is progressed by heating leading to plastic deformation and recrystallization by cooling. The above procedure is carried out once or repeated multiple times, thereby obtaining a desired average crystal grain size.

According to aspects of the invention, the device formed from the metal material provided herein has a nanostructure not limited to the surface. For example, the metal material can keep its nanostructure throughout its processing resulting in a metal material having a homogeneous nanostructure.

According to some embodiments, the magnetic fields of the metal material provided herein can alter surface charges as well as initial protein adsorption events to in turn change bacteria attachment and colonization and/or growth of eukaryotic cells.

Polish/Unpolish Metal Material

In some embodiments, the metal material can be polished to change the surface roughness. In some embodiments, the method of polishing the metal material comprises rough polishing using lapping film (see Example 4).

The surface roughness can be calculated with an atomic force microscope (AFM) and three different parameters can be obtained for the metal material—the root mean square roughness (Rq), the arithmetic roughness (Ra) and the maximum height (Rz).

TABLE 1

| Polish Samples | Rq (nm) | Ra (nm) | Rz (nm) |
|---|---|---|---|
| 304-0.5 | 2.218 | 1.605 | 24.180 |
| 304-1.5 | 2.729 | 2.006 | 119.350 |
| 304-9 | 2.391 | 1.750 | 4.490 |
| 316-1.5 | 2.376 | 1.809 | 52.760 |
| 316-10 | 2.606 | 2.044 | 77.020 |

TABLE 2

| Non-polish Samples | Rq (nm) | Ra (nm) | Rz (nm) |
|---|---|---|---|
| 304-0.5 | 5.978 | 4.654 | 54.790 |
| 304-1 | 8.725 | 6.962 | 60.926 |
| 304-1.5 | 6.183 | 4.864 | 49.116 |
| 304-2 | 7.138 | 5.706 | 49.938 |
| 304-3 | 6.633 | 4.872 | 76.560 |
| 304-9 | 3.630 | 2.868 | 29.778 |
| 316-1.5 | 9.923 | 7.797 | 77.923 |
| 316-10 | 8.660 | 6.587 | 72.594 |

In some embodiments, the material is polished has a surface roughness at the nanoscale from about 0.1 nm to 100 μM.

Previous studies showed that the optimal value of surface energy to inhibit bacteria growth is around 42 N/m, (See Liu et al., "Understanding the Role of Polymer Surface Nanoscale Topography on Inhibiting Bacteria Adhesion and Growth" Biomaterials Science and Engineering, 2016, 2 (1), pp 122-130.)

In some embodiments, the value of surface energy of the metal material is between 40 to 45 N/m, 40-47 N/m, 40 and 50 N/m, 40 to 55 N/m, 40 to 60 N/m, 35 to 45 N/m, 35 to 50 N/m, 35 to 55 N/m, 35 to 60 N/m, 30 to 45 N/m, 30 to 50 N/m, 30 to 55 N/m, 30 to 60 N/m.

In some embodiments, the metal material described herein has a surface energy that promotes growth of some eukaryotic cells. Yet in some embodiments, the metal material described herein has a surface energy that inhibits growth of other eukaryotic cells. For example, the surface energy can promote the attachment and the growth of endothelial cells and inhibit the attachment and/or growth of fibroblast.

In some embodiments, the value of surface energy of the metal material to promote growth of eukaryotic cells is between 40 to 45 N/m, 40-47 N/m, 40 and 50 N/m, 40 to 55 N/m, 40 to 60 N/m, 35 to 45 N/m, 35 to 50 N/m, 35 to 55 N/m, 35 to 60 N/m, 30 to 45 N/m, 30 to 50 N/m, 30 to 55 N/m, 30 to 60 N/m.

Optimal Ra, Rq, Rz can be calculated with the Khang's equation using 45 N/m for the ideal surface energy.

$$Es = E0, +\rho \times reff$$

ES=surface energy

Eo,s=ground Surface energy reff=roughness

ρ=coupling constant

In some embodiments, the metal material can have a surface energy tailored to the adsorption of proteins that decrease inflammatory cell functions, decrease bacterial functions, increase bone cell functions, increase endothelial cell functions or any combinations of the foregoing.

In some embodiments, the metal material can have an average grain size tailored to the adsorption of proteins that decrease inflammatory cell functions, decrease bacterial functions, increase bone cell functions, increase endothelial cell functions or any combinations of the foregoing.

In some embodiments, the metal material can be polished or unpolished. In some embodiments, the polished and/or unpolished metal material has an average grain size is between about 100 nm and 10 μm, for example less than 500 nm for decreasing attachment or growth of both gram positive and negative bacteria. In some embodiments, the polished and/or unpolished metal material has an average grain size is preferably between about 3 and 7 μm.

Shape/Devices

The shape of the metal material according to some embodiments is not particularly limited, and any shape such as a plate shape, a line shape, a rod shape, a spherical shape or a cylindrical shape can be adopted. In some embodiments, the metal material is in the shape of a wire or line.

In some embodiments, the metal material is in the form of a plate or foil with a thickness ranging from about 0.1 mm to 1 mm, from example 0.1 mm, 0.2 mm, 0.3 mm, 0.4 mm, 0.5 mm, 0.5 mm, 0.6 mm, 0.7 mm, 0.8 mm, 0.9 mm, or 1 mm.

In some embodiments, the metal material is in the form of a bar or wire with a dimeter of from 0.02 mm to 6 mm.

Method of Inhibiting Growth of Microorganism

The method of inhibiting growth of microorganism according to some embodiments is a method using the metal material including the predetermined average crystal grain.

In some embodiments, a metal material, for example, a stainless steel material, is provided in which each average crystal grain size of crystal grains is adjusted within a range of from 0.1 μm to 20 μm, from 0.5 μm to 20 μm, from 1 μm to 20 μm, from 2 μm to 20 μm, from 3 μm to 20 μm, from 4 μm to 20 μm, from 5 μm to 20 μm, from 6 μm to 20 μm, from 7 μm to 20 μm, from 8 μm to 20 μm, from 9 μm to 20 μm, from 10 μm to 20 μm, from 11 μm to 20 μm, from 12 μm to 20 μm, from 13 μm to 20 μm, from 14 μm to 20 μm, from 15 μm to 20 μm, from 16 μm to 20 μm, from 17 μm to 20 μm, from 18 μm to 20 μm, from 19 μm to 20 μm, 0.1 μm to 10 μm, from 0.5 μm to 10 μm, from 1 μm to 10 μm, from 2 μm to 10 μm, from 3 μm to 10 μm, from 4 μm to 10 μm, from 5 μm to 10 μm, from 6 μm to 10 μm, from 7 μm to 10 μm, from 8 μm to 10 μm, from 9 μm to 10 μm, from 1 μm to 2 μm, from 2 μm to 3 μm, from 3 μm to 4 μm, from 4 μm to 5 μm, from 5 μm to 6 μm, from 6 μm to 7 μm, from 7 μm to 8 μm, from 8 μm to 9 μm, about 0.5 μm, about 1 μm, about 2 μm, about 3 μm, about 4 μm, about 5 μm, about 6 μm, about 7 μm, about 8 μm, about 9 μm, or about 10 μm or higher. In some embodiments, the average crystal grain size is greater than 0.5 μm but smaller than 10 μm. In some embodiments, the average crystal grain size is greater than 0.5 μm but smaller than 7 μm. In some embodiments, the average crystal grain size is greater than 1 μm but smaller than 7 μm. In some embodiments, the average crystal grain size is greater than 3 μm but smaller than 7 μm.

In some embodiments, the average crystal grain size of the crystal grain for giving the optimal inhibition for microorganism growth is determined based on the response profile obtained in the above procedure.

Figure 1B:
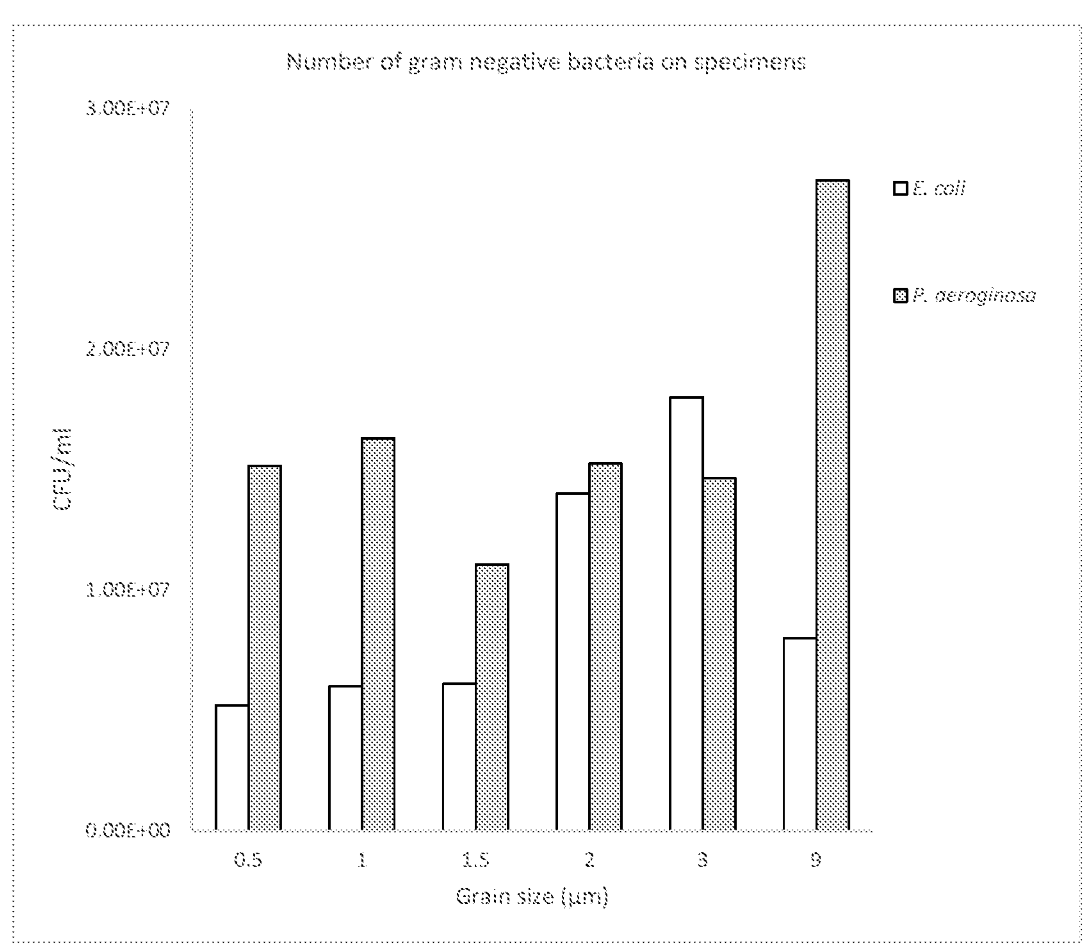
FIG. 1B is an example of a response profile obtained by plotting a response amount (CFU/ml) of gram negative bacteria (*E. coli, P. aeruginosa*) with respect to an average crystal grain size of a crystal grain according to some embodiments.

FIG. 1A shows antibiotic properties of the metal material on gram positive bacteria. For example, FIG. 1A shows that metal material having a grain size of 0.5 μm, 1 μm, 1.5 μm, 3 μm and 9 μm inhibits growth/adhesion of gram positive bacteria. FIG. 1B shows antibiotic properties of the metal material on gram negative bacteria. For example, FIG. 1B shows that metal material having a grain size of 0.5, 3 and 9 μm inhibits growth/adhesion of gram positive bacteria.

Methods of Using to Promoting or Inhibit Cell Adhesion and/or Growth

In some embodiments, the devices can be implanted at the following anatomical locations: subcutaneous, intraperitoneal, intramuscular, intravascular, intraocular, intracerebral or other appropriate sites.

In some embodiments, the nanostructure of the metal material can be tailored to match proteins at the nanometer scale and cells at the micrometer scale. In some embodiments, the crystal grain size can facilitate adhesion of endothelial cells or osteoblast.

In some embodiments, implantable metallic devices are provided having 2 or more surfaces. In some embodiments, the device can comprise a first metal surface configured to have a surface energy that promotes the attachment and/or the growth of a first cell type and a second surface configured to have a surface energy to inhibit the attachment and/or the growth of a second, different cell type. In some embodiments, the device can comprise a first metal surface configured to have an average grain size that promotes the attachment and/or the growth of a first cell type and a second surface configured to have an average grain size to inhibit the attachment and/or the growth of a second, different cell type. For example, the implantable device can be a vascular stent having a first surface configured to promote the attachment and/or the growth of endothelial cells and a second surface configured to inhibit the attachment and/or the growth of fibroblast.

In some embodiments, the metal material can have an average grain size and/or surface energy that inhibit attachment of the cells, growth of the cells or combinations thereof. For example, the metal material can inhibit attachment and/or growth of cells responsible for inflammation, such as immune cells.

EXAMPLES

Hereinafter, the present invention will be described in detail with reference to examples, but the present invention is not limited to the following examples unless it exceeds the gist of the present invention.

Example 1: Manufacture of Metal Material

In order to provide metal materials, stainless steel (SUS 304) was subjected to rolling treatment and thermal recrystallization to adjust the average crystal grain sizes of crystal grains to 0.5 μm, 1 μm, 1.5 μm, 2 μm, 3 μm, and 9 μm, respectively. The metal material had a plate shape having a length of 10 mm, a width of 10 mm, and a thickness of 0.1 mm. The rolling treatment and thermal recrystallization were carried out according to the following procedure. Specifically, the stainless steel (SUS 304) was passed through a rotating mill several times and cold-rolled to about 40 to 65% (compression ratio of about 3 to 15% per time). Then, the resulting stainless steel was subjected to annealing at 600 to 850° C. for 10 to 100 seconds (heating rate: 200° C./sec) to recrystallize the stainless steel. Depending on the state of phase transformation, the recrystallized stainless steel was cooled to obtain an austenitic stainless steel (cooling rate: 200 to 400° C./sec.).

It should be appreciated that type 316 stainless steel and other metals can be subjected to the same process to control the average grain size.

Example 2—Measurement of Average Crystal Grain Size

The test sample of the metal material provided above was polished with argon ions using an ion polisher ("IM 4000", manufactured by Hitachi High-Technologies Corporation). Thereafter, the average crystal grain size of the metal material was measured at room temperature in a vacuum environment ($1\times10^{-3}$ Pa) using an electron microscope ("SU-70", manufactured by Hitachi High-Technologies Corporation) having a crystal orientation analysis function. The size of each crystal grain was determined by determining the area of each crystal grain in an arbitrary measurement range (i.e., the observed image; magnification: 1000 times) and calculating a diameter of a circle, assuming that the shape of the crystal grain is a circle having the same area as the area of the crystal grain. The area of the crystal grain and the diameter of the circle having the same area as the area of the crystal grain were calculated using an image processor ("TSL OMI Analysis 7", manufactured by TSL Solutions). Then, the sum of all crystal grain diameters in the arbitrary measurement range was divided by the number of crystal grains, and the resulting value was defined as an average crystal grain size (nm).

Example 3—Antibiotic Properties of Unpolished Metal Material

Methods:

The bacteria were first incubated overnight. After reaching a concentration of $10^5$, the bacteria were mixed with the metal material samples (type 304 stainless steel samples) and incubated for 24 hours. The type 304 stainless steel samples were then washed with distilled water and sonicated for 10 min. After vortexing the samples for an extra 10 seconds, several dilutions of each sample were placed on gar plates. The agar plates were incubated for 12 hours.

Results:

FIG. 1A and FIG. 1B each show an example of the response profile obtained by plotting the colony-forming unit of the gram positive or gram-negative bacteria after cultivation with respect to the average crystal grain size of the crystal grain.

As shown in FIG. 1A, the number of gram positive bacteria adsorbed on the metal materials was relatively decreased when the average grain size was 0.5 μm, 1 μm, 1.5 μm, 3 μm and 9 μm showing that the metal materials tested inhibits growth/adhesion of gram positive bacteria. As shown in FIG. 1B the number of bacteria adsorbed on the metal materials was relatively decreased when the average grain size was 0.5 μm, 3 μm and 9 μm showing that the metal materials tested inhibits growth/adhesion of gram negative bacteria.

Example 4—Antibiotic Properties of Unpolished Metal Material Versus Polished Material Antibiotics properties of unpolished metal material vs polished material were measured.

Methods:

Specimen: Type 304 stainless steel as shown in Table 3: diameter (ϕ) 11 mm; thickness: 0.1 mm.

TABLE 3

| material | grain size (μm) | C (W %) | Si (W %) | Mn (W %) | P (W %) | S (W %) | Ni (W %) | Cr (W %) |
|---|---|---|---|---|---|---|---|---|
| 304 | 0.5<br>1.0<br>1.5<br>2.0<br>3.0<br>9.0 | 0.05 | 0.39 | 1.10 | 0.030 | 0.004 | 8.03 | 18.01 |

In a first step the specimen was subjected to rough polishing using 3M lapping film whetstone alumina.

The specimen was first polished using a 3M lapping film mesh No. 4000 (3 μm) on the five papers for approximately 40 seconds with hand. The specimen was then polished with a 3M lapping film mesh No. 8000 (1 μm) for approximately 40 seconds with hand. The specimen was then polished with a 3M lapping film mesh No. 15000 (0.3 μm) for approximately 40 seconds with hand.

In a second step the specimen was alumina polished using an alumina solution and buffed using grinding machine on table. The alumina solution used is a mixture solution of φ1 μm alumina and ϕ0.05 μm alumina (ϕ1 μm alumina: Buehler Micro Polish II Alumina 1.0 μm; ϕ0.05 μm alumina: BuehlerMasterPrep Polishing Suspension 0.05 μm).

Figure 10:
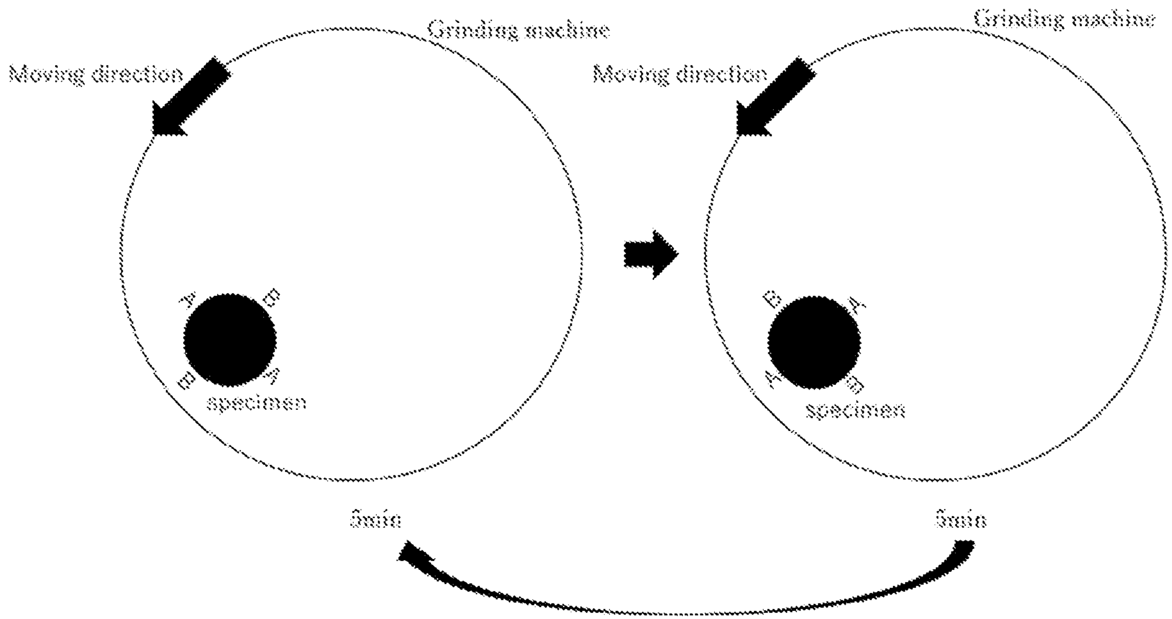
FIG. 10 is a schematic of a polishing method according to some embodiments.

The specimen was polished for five minutes with keeping a first direction A, five minutes with keeping a second direction B five minutes with keeping the direction A and five minutes with keeping the direction B, for a total of 20 minutes polishing as shown on FIG. 10.

In a third step, the specimen was washed with: (1) first with water: first the specimen was washed with hand softly in diluted neutral detergent and tap water, then with running water from bibcock, then the specimen was softly wiped to dry the specimen; (2) then with ethanol by placing the specimen in ethanol and pulling out the specimen and wiping softly to keep specimen to dry the specimen.

Figure 2A:
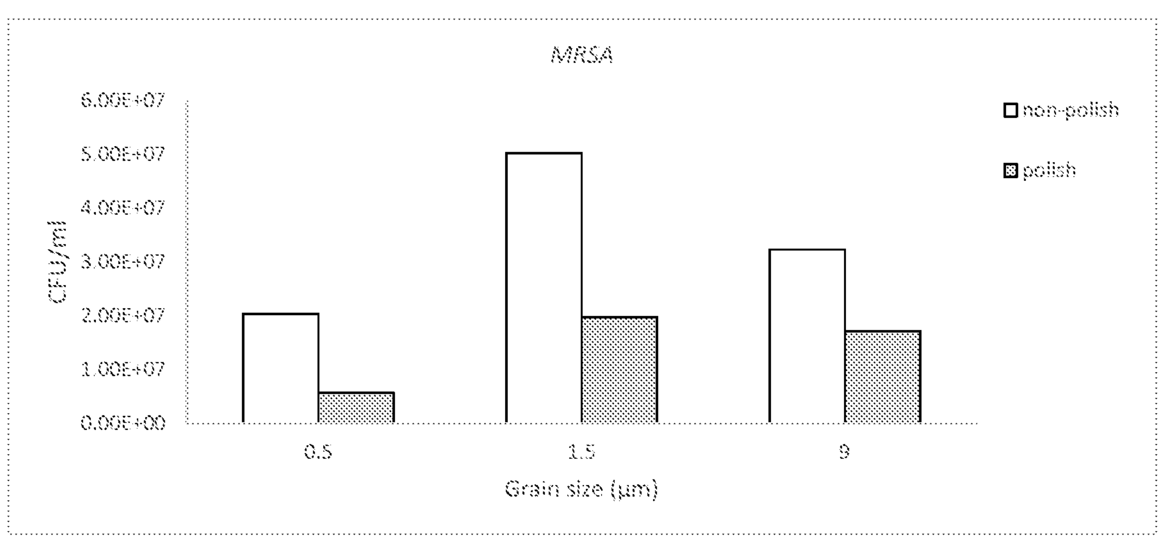
FIG. 2A is an example of a response profile obtained by plotting a response amount (CFU/ml) of gram positive bacteria MRSA with respect to an average crystal grain size polished or unpolished of a crystal grain according to some embodiments.
Figure 2B:
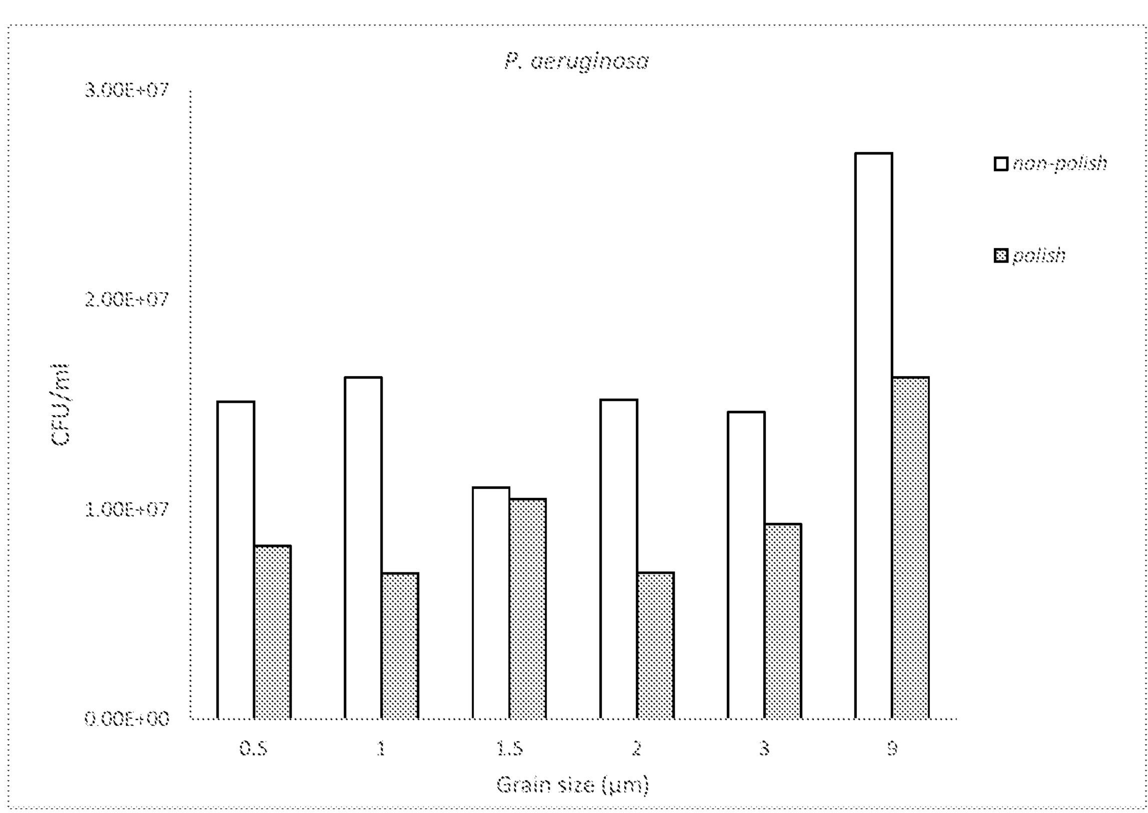
FIG. 2B is an example of a response profile obtained by plotting a response amount (CFU/ml) of gram negative bacteria *P. aeruginosa* with respect to an average polished or unpolished crystal grain size of a crystal grain according to some embodiments.

FIG. 2A and FIG. 2B show that the number of bacteria adsorbed on the metal materials with an average grain size was 0.5, 1, 1.5, 2, 3 and 9 μm was relatively decreased when the metal material was polished.

Example 5—Cytotoxicity MTS Assay

Methods:

Human fetal osteoblasts (HFOb) were seeded in 12 wells plates with the metal material samples. Cell media was changed every 2 days. For the cell proliferation assay, MTS reagent was added after 3, 5, and 7 days to determine the number of cells alive.

Figure 3A:
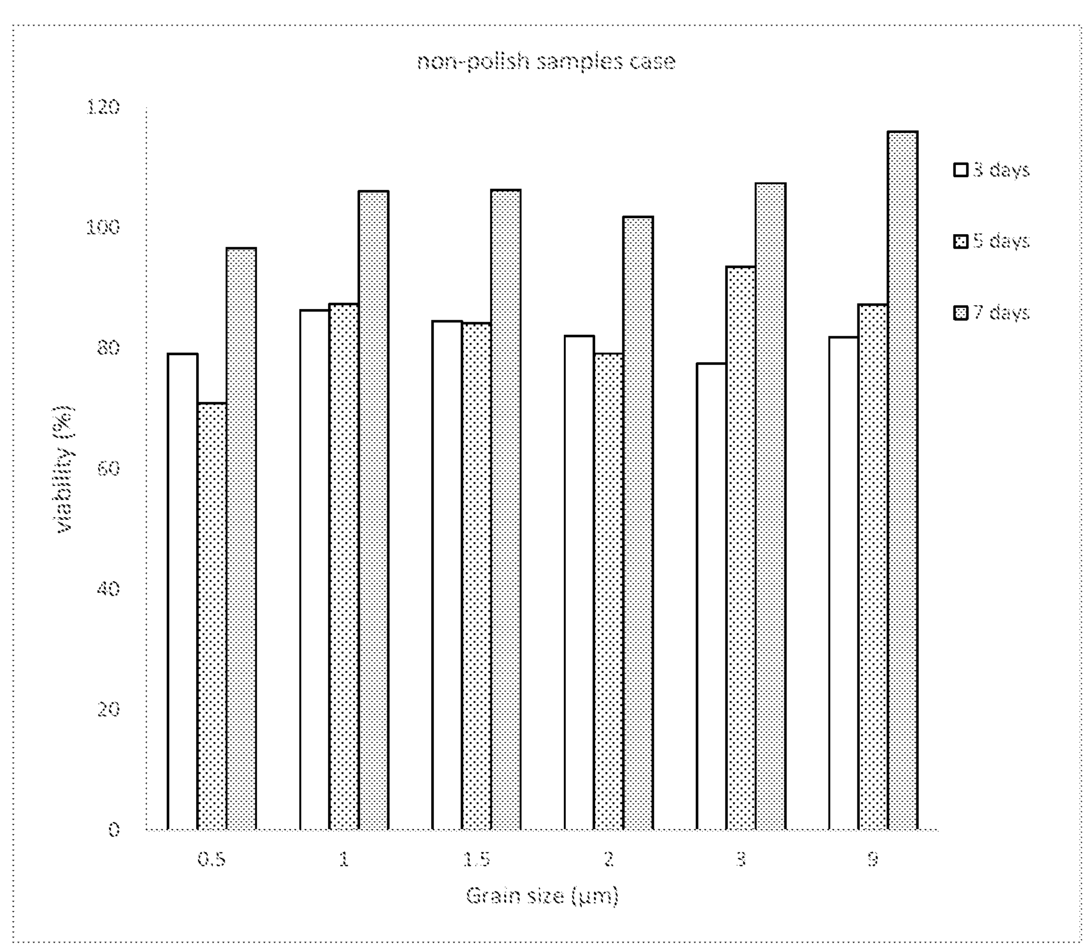
FIG. 3A is an example of a response profile obtained by plotting viability of osteoblast cells with respect to an average unpolished crystal grain size of a crystal grain according to some embodiments.
Figure 3B:
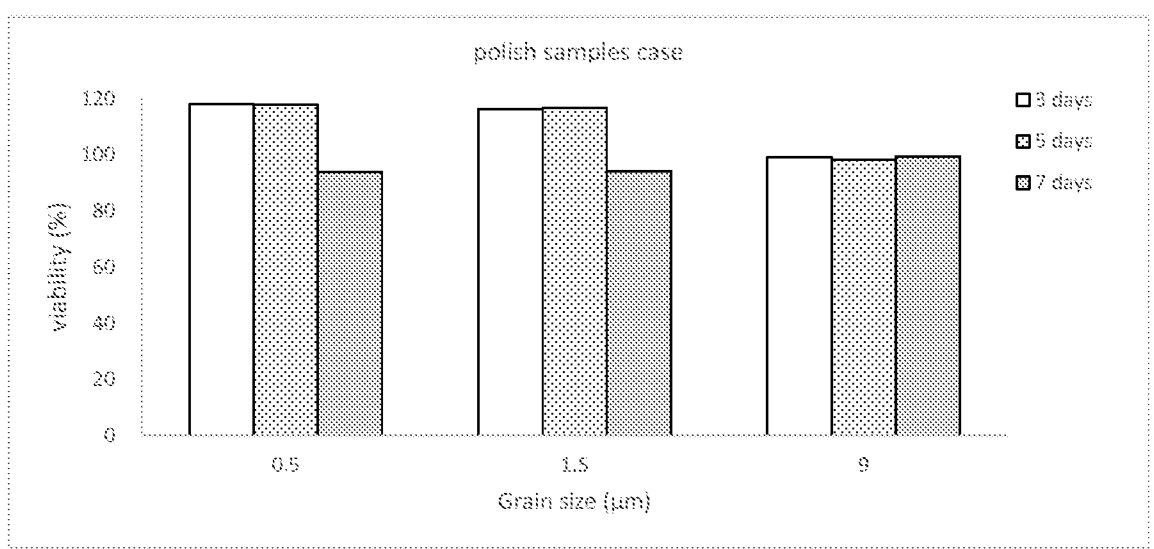
FIG. 3B is an example of a response profile obtained by plotting viability of osteoblast cells with respect to an average polished crystal grain size of a crystal grain according to some embodiments.

Results:

FIG. 3A and FIG. 3B show that the metal material has no cytotoxicity. For most of the samples, the viability was 80% or higher for all three readings (3, 5, and 7 days). For day 7, all readings showed a viability of 100% or higher. Higher viability showed that the metal material samples promoted cell growth.

For polished samples, all the readings showed a cell viability between 90% and 120%. For day 5, all the samples presented a cell viability higher than 100% showing that the metal material samples promoted cell growth. Non-polished samples presented a greater cell viability than polish samples. Metal material having an average grain size of 9 μm showed the greatest viability on non-polished samples.

Example 6: Antibiotic Property of Type 316 Stainless Steel on Bacteria Colony-Forming Unit in Relationship of Average Grain Size—Predictive Equations Methods:

The bacteria were first incubated overnight. After reaching a concentration of $10^5$, the bacteria were mixed with the metal material samples and incubated for 24 hours. The samples were then washed with distilled water and sonicated for 10 min. After vortexing the samples for an extra 10 seconds, several dilutions of each sample were placed on gar plates. The agar plates were incubated for 12 hours.

The chemical composition of the type 316 stainless steel metal samples used is shown in the Table 4 below:

TABLE 4

| type | Diameter (mm) | C | Si | Mn | P | S | Ni | Cr | Mo |
|---|---|---|---|---|---|---|---|---|---|
| CG | 0.8 | 0.03 | 0.58 | 1.05 | 0.026 | 0.001 | 12.08 | 17.62 | 2.07 |
| | 0.4 | 0.040 | 0.50 | 1.04 | 0.029 | 0.001 | 12.10 | 17.44 | 2.02 |
| | 0.2 | 0.020 | 0.42 | 1.33 | 0.029 | 0.001 | 10.10 | 16.00 | 2.00 |
| UFGSS | 0.8 | 0.03 | 0.39 | 1.04 | 0.027 | 0.001 | 11.56 | 17.38 | 2.03 |
| | 0.4 | 0.03 | 0.39 | 1.04 | 0.027 | 0.001 | 11.56 | 17.38 | 2.03 |
| | 0.2 | 0.03 | 0.39 | 1.04 | 0.027 | 0.001 | 11.56 | 17.38 | 2.03 |

The metal samples tested were type 316 stainless steel wires having different diameters (φ in mm) and different average grain sizes (in μm). Ultrafine average grain size (UGCSS) vary from 0.18 μm to 0.25 μm and conventional grain size vary from 7.1 μm to 16.5 μm.

CG316 φ0.8 grain size 16.5 μm
CG316 φ0.4 grain size 10.7 μm
CG316 φ0.2 grain size 7.1 μm
UFGSS 316 φ0.8 grain size 0.25 μm
UFGSS 316 φ0.4 grain size 0.22 μm
UFGSS 316 φ0.2 grain size 0.18 μm Results:

For the conventional grain (CG) samples, the CFU/ml of *S. aureus*, MRSA and *E. coli* on the type 316 stainless steel metal materials was relatively decreased when the average grain size was 7.1 μm compared to when the average grain size was 10.7 or 16.5 μm. In contrast the number of *P. aeruginosa* the CFU/ml on the type 316 stainless steel metal materials was relatively decreased when the average grain size was 16.5 μm compared to when the average grain size was 7.1 or 10.7 μm due to the corresponding change in surface energy.

For the ultrafine (UF) samples, the CFU/ml of *S. aureus*, MRSA and *E. coli* on the type 316 stainless steel metal materials was relatively decreased when the average grain size was 0.18 μm compared to when the average grain size was 0.22 or 0.25 μm. In contrast the number of *P. aeruginosa* the CFU/ml on the type 316 stainless steel metal materials was relatively decreased when the average grain size was 0.25 μm compared to when the average grain size was 0.18 or 0.22 μm due to the corresponding change in surface energy.

Without being bound to the theory, changes in surface energy in turn can change initial protein adsorption and confirmation events to inhibit bacteria attachment and colonization.

Predictive equations and optimal grain size were calculated.

FIGS. 4A-4D show are examples of the response profile obtained by plotting the colony-forming unit of the gram positive or gram-negative bacteria after cultivation with respect to the average crystal grain size of the crystal grain.

Figure 4A:
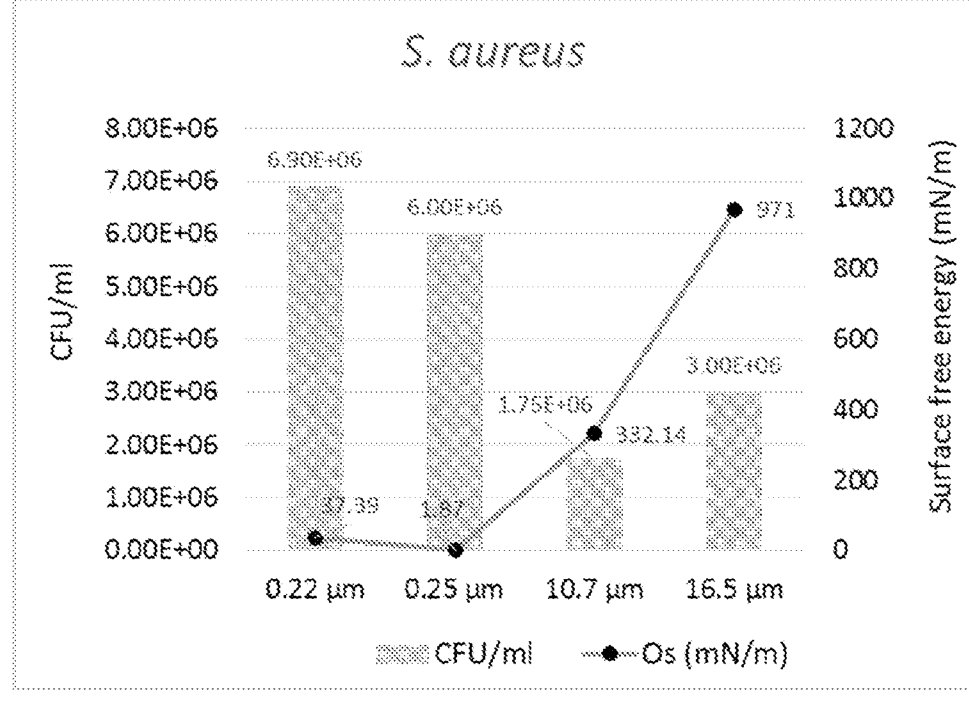
FIG. 4A is an example of a response profile obtained by plotting a response amount (CFU/ml) and surface free energy (mN/m) of *S. aureus* bacteria with respect to an average crystal grain size of a crystal grain according to some embodiments.
Figure 4B:
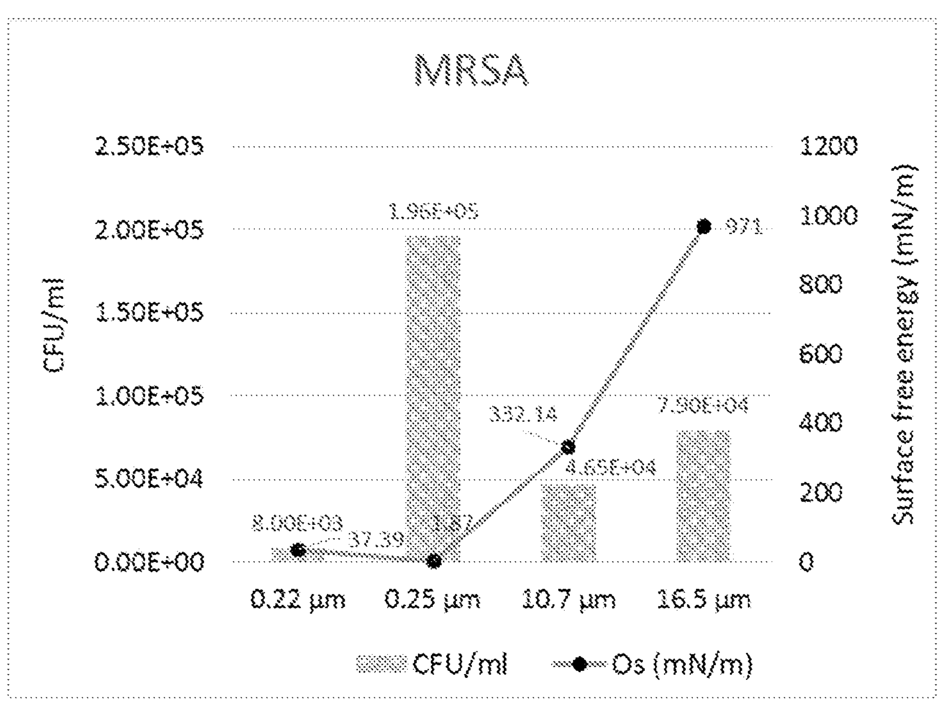
FIG. 4B is an example of a response profile obtained by plotting a response amount (CFU/ml) and surface free energy (mN/m) of Methicillin-resistant *Staphylococcus aureus* bacteria (MRSA) with respect to an average crystal grain size of a crystal grain according to some embodiments.
Figure 4C:
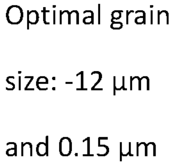
FIG. 4C is an example of a response profile obtained by plotting a response amount (CFU/ml) and surface free energy (mN/m) of *E. coli* bacteria with respect to an average crystal grain size of a crystal grain according to some embodiments.
Figure 4C:
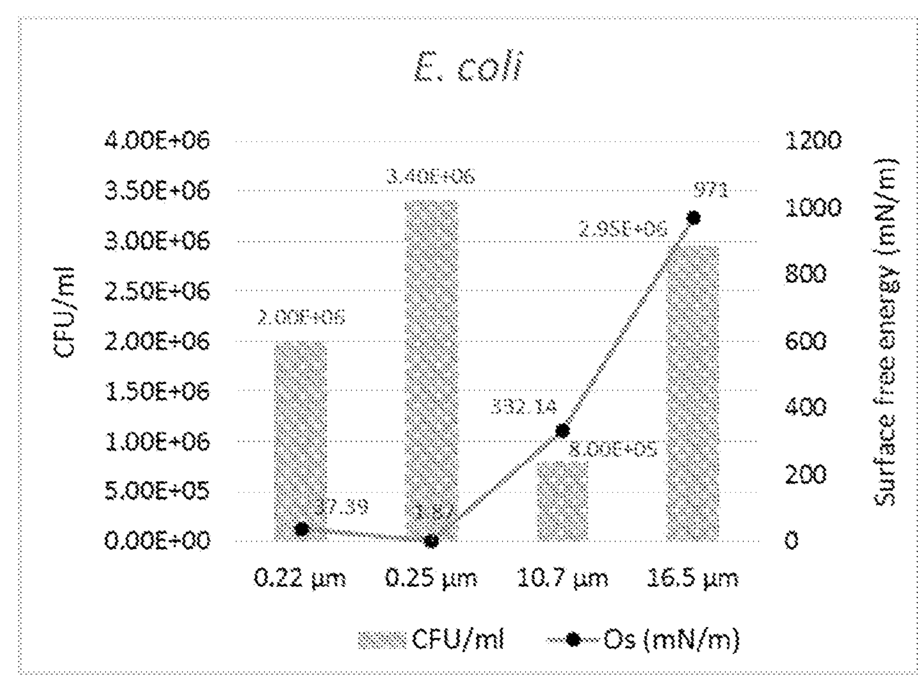
Figure 4D:
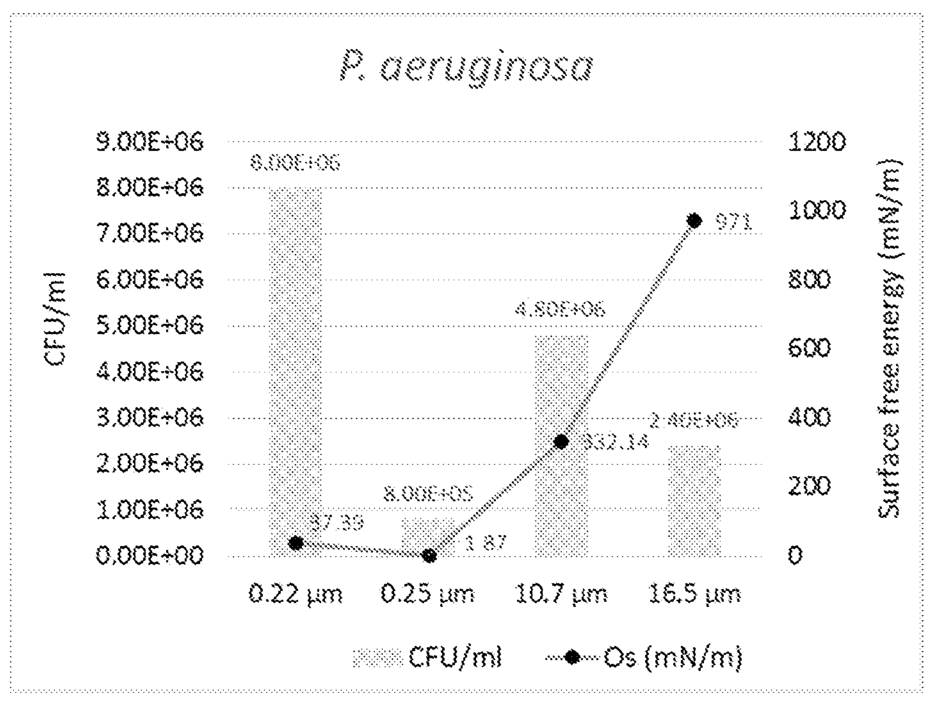
FIG. 4D is an example of a response profile obtained by plotting a response amount (CFU/ml) and surface free energy (mN/m) of *P. aeruginosa* bacteria with respect to an average crystal grain size of a crystal grain according to some embodiments.

FIG. 4A shows the predictive equations for calculating the optimal grain size to inhibit growth/adhesion of *S. aureus* for conventional grain and ultrafine grain type 316 stainless steel metal material. FIG. 4B shows the equation for calculating the optimal grain size to inhibit growth/adhesion of MRSA for conventional grain and ultrafine grain type 316 stainless steel metal material. FIG. 4C shows the equation for calculating the optimal grain size to inhibit growth/adhesion of *E. coli* for conventional grain and ultrafine grain type 316 stainless steel metal material. FIG. 4D shows the equation for calculating the optimal grain size to inhibit growth/adhesion of *P. aeruginosa* for conventional grain and ultrafine grain type 316 stainless steel metal material.

As shown in FIGS. 4A-4D, the CFU/ml for the bacteria tested ranges from 0.125 μm to 19.02 μm.

FIGS. 4A-4C showed that the number of bacteria *S. aureus*, MRSA and *E. coli* adsorbed on the metal materials was relatively decreased when the average grain size of the conventional grain size samples was 10.7 μm.

The predictive equations for conventional grain metal material showed that the predicted optimal average grain size to inhibit MRSA and *E. coli* growth/absorption ranges from 4.28 μm to 19.02 μm.

The predictive equations for ultrafine grain metal material showed that the predicted optimal average grain size to inhibit *S. aureus*, MRSA, *E. coli* and *P. aeruginosa* growth/absorption ranges from 0.125 μm to 0.33 μm.

Example 7: Antibiotic Property of Type 316 Stainless Steel on Bacteria Colony-Forming Unit Normalized to Surface Area in Relationship of Average Grain Size—Predictive Equations The antibiotic effect of type 316 stainless steel on bacteria CFU was obtained using the metal material samples and the methods of Example 6.

The CFU unit was normalized to the surface area using the table 5 shown below:

TABLE 5

| | | | |
|---|---|---|---|
| Diameter samples (mm) | 0.2 | 0.4 | 0.8 |
| Area samples ($mm^2$) | 8.04 | 16.21 | 32.92 |

Results:

For the coarse grain (CG) samples, the CFU/ml of *S. aureus*, MRSA and *P. aeruginosa* on the type 316 stainless steel metal materials was relatively decreased when the average grain size was 16.5 μm compared to when the average grain size was 10.7 μm. In contrast the number of *E. coli* the CFU/ml on the type 316 stainless steel metal materials was relatively decreased when the average grain size was 10.7 μm compared to when the average grain size was 16.5 μm.

For the ultrafine (UF) samples, the CFU/ml of *S. aureus, E. coli* and *P. aeruginosa* on the type 316 stainless steel metal materials was relatively decreased when the average grain size was 0.25 μm compared to when the average grain size was 0.22 μm. In contrast the number of MRSA the CFU/ml on the type 316 stainless steel metal materials was relatively decreased when the average grain size was 0.22 μm compared to when the average grain size was 0.25 μm.

Predictive equations and optimal grain size were calculated.

Figure 5A:
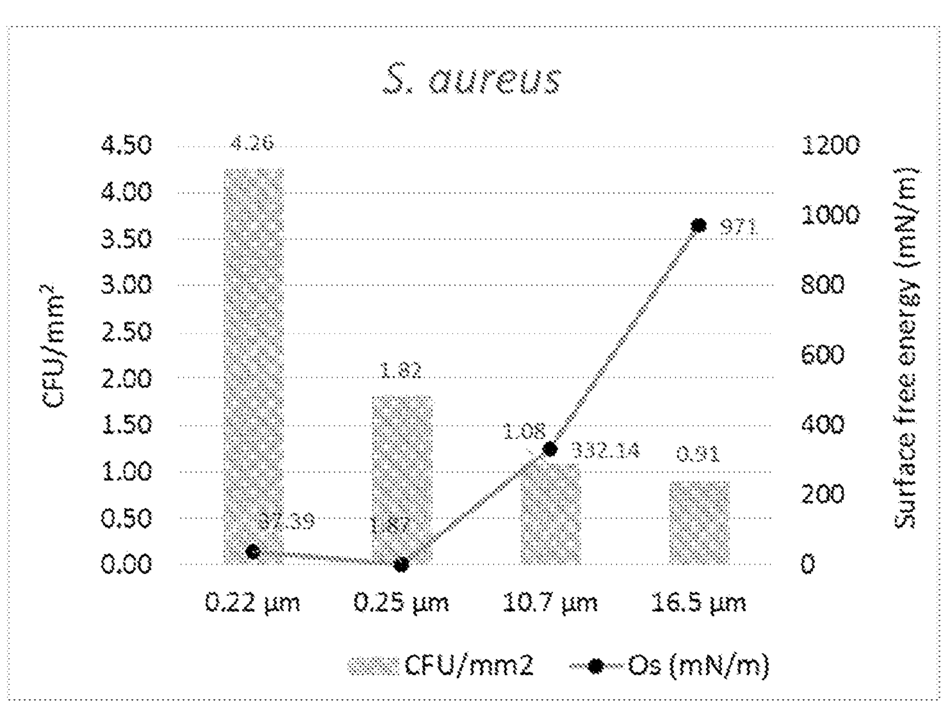
FIG. 5A is an example of a response profile obtained by plotting a response amount (CFU/ml) and surface free energy (mN/m) normalized to surface area of *S. aureus* bacteria with respect to an average crystal grain size of a crystal grain of type 316 stainless steel according to some embodiments.

FIGS. 5A-4D show exemplary response profile obtained by plotting the colony-forming unit of the gram positive or gram-negative bacteria after cultivation with respect to the average crystal grain size of the crystal grain.

Figure 5B:
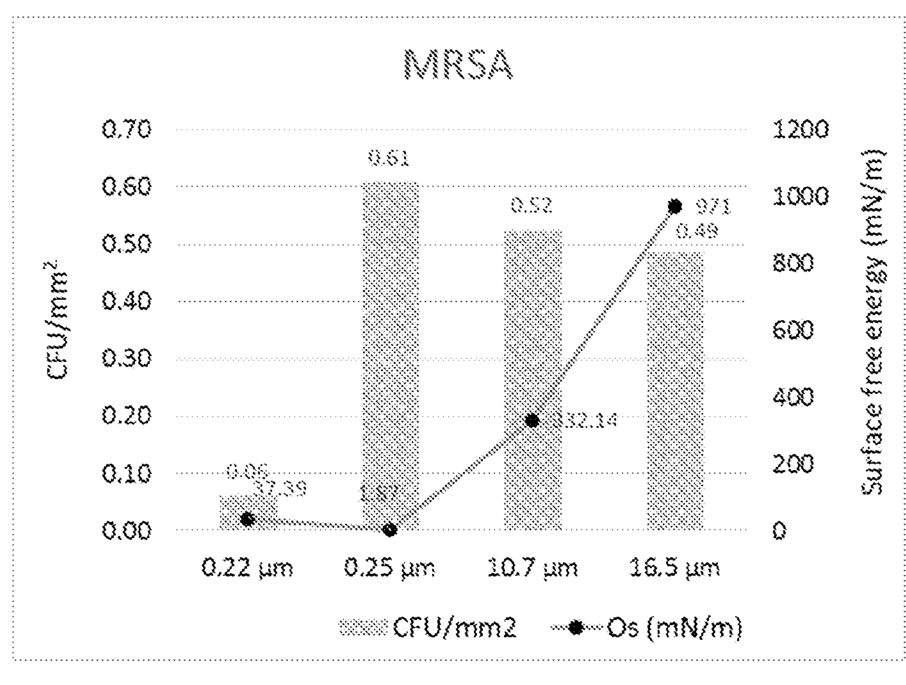
FIG. 5B is an example of a response profile obtained by plotting a response amount (CFU/ml) and surface free energy (mN/m) normalized to surface area of Methicillin-resistant *Staphylococcus aureus* bacteria with respect to an average crystal grain size of a crystal grain of type 316 stainless steel according to some embodiments.
Figure 5C:
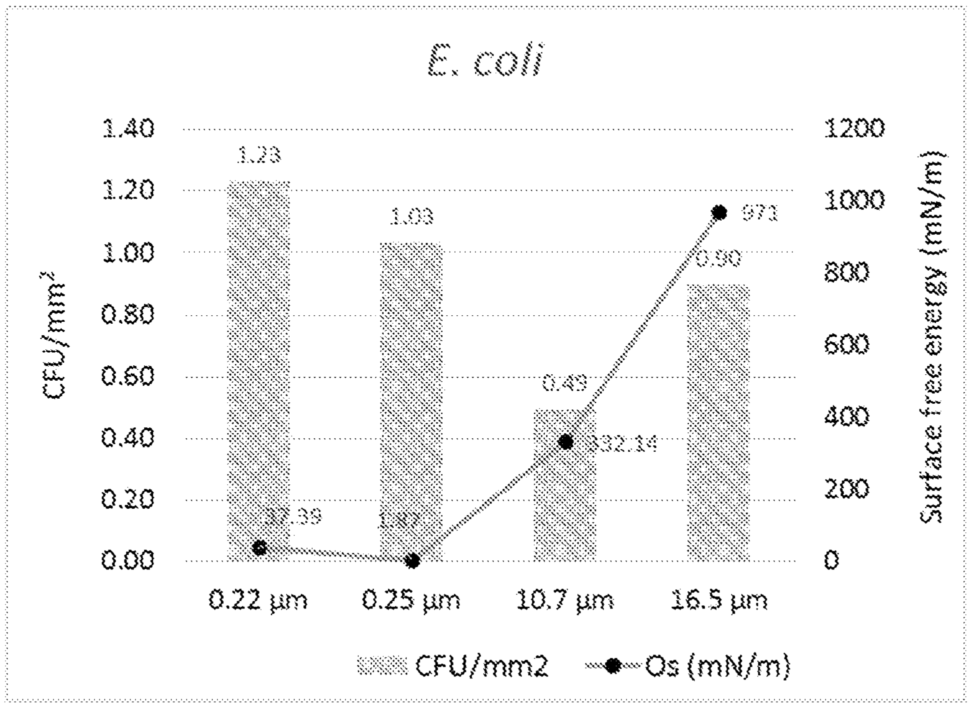
FIG. 5C is an example of a response profile obtained by plotting a response amount (CFU/ml) and surface free energy (mN/m) normalized to surface area of *E. coli* bacteria with respect to an average crystal grain size of a crystal grain of type 316 stainless steel according to some embodiments.
Figure 5D:
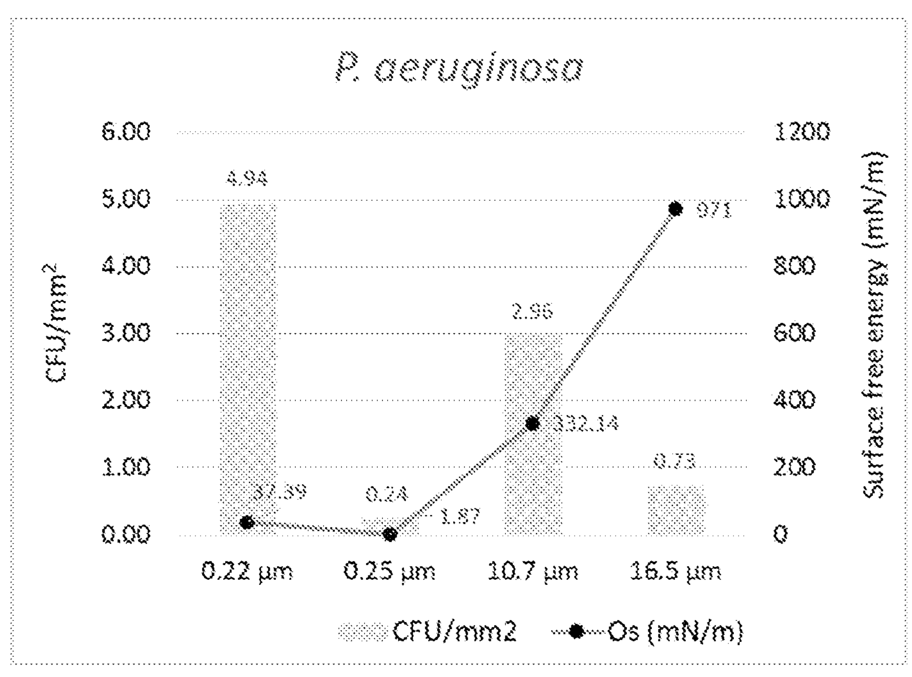
FIG. 5D is an example of a response profile obtained by plotting a response amount (CFU/ml) and surface free energy (mN/m) normalized to surface area of *P. aeruginosa* bacteria with respect to an average crystal grain size of a crystal grain of type 316 stainless steel according to some embodiments.

FIG. 5A shows the predictive equations for calculating the optimal grain size to inhibit growth/adhesion of *S. aureus* for conventional grain and ultrafine grain type 316 stainless steel metal material. FIG. 5B shows the equation for calculating the optimal grain size to inhibit growth/adhesion of MRSA for conventional grain and ultrafine grain type 316 stainless steel metal material. FIG. 5C shows the equation for calculating the optimal grain size to inhibit growth/adhesion of *E. coli* for conventional grain and ultrafine grain type 316 stainless steel metal material. FIG. 5D shows the equation for calculating the optimal grain size to inhibit growth/adhesion of *P. aeruginosa* for conventional grain and ultrafine grain type 316 stainless steel metal material.

As shown in FIGS. 5A-5D, the CFU/ml normalized to surface area for the bacteria tested ranges from 0.04 μm to 25.71 μm.

FIGS. 5A, 5B and 5D showed that the number of bacteria *S. aureus*, MRSA and *P. aeruginosa* adsorbed on the conventional grain size metal materials tested was relatively decreased when the average grain size of the conventional grain size metal samples was 16.5 μm as compared to 10.7 μm. In contrast, FIG. 5C showed that the number of *E. coli* bacteria adsorbed on the conventional grain size metal materials tested was relatively decreased when the average grain size of the conventional grain size metal samples was 10.7 μm as compared to 15.5 μm due to the corresponding change in surface energy.

FIGS. 5A, 5B and 5D showed that the number of bacteria *S. aureus*, MRSA and *P. aeruginosa* adsorbed on the ultrafine grain size metal materials tested was relatively decreased when the average grain size of the ultrafine grain size metal samples was 0.25 μm as compared to 0.22 μm. In contrast, FIG. 5C showed that the number of *E. coli* bacteria adsorbed on the ultrafine grain size metal materials tested was relatively decreased when the average grain size of the ultrafine grain size metal samples was 0.25 μm as compared to 0.22 μm due to the corresponding change in surface energy.

The predictive equations of FIGS. 5A, 5B and 5D showed that the predicted optimal average grain size of the conventional grain size metal samples to inhibit *S. aureus, E. coli* and *P. aeruginosa* growth/absorption ranges from 16.46 μm to 25.71 μm.

The predictive equations of FIGS. 5A, 5B and 5D showed that the predicted optimal average grain size of the ultrafine grain size metal samples to inhibit *S. aureus*, MRSA and *P. aeruginosa* growth/absorption ranges from 0.004 and 0.28 μm.

Example 8—Antibiotic Property of Type 304 Stainless Steel on Bacteria Colony-Forming Unit Normalized to Surface Area in Relationship of Average Grain Size—Predictive Equations Methods:

The bacteria were first incubated overnight. After reaching a concentration of $10^5$, the bacteria were mixed with the metal material samples and incubated for 24 hours. The samples were then washed with distilled water and sonicated for 10 min. After vortexing the samples for an extra 10 seconds, several dilutions of each sample were placed on gar plates. The agar plates were incubated for 12 hours.

The chemical composition of the type 316 stainless steel metal is shown in Example 6. The chemical composition of the type 304 stainless steel metal samples used is shown in the table 6 below:

TABLE 6

| type | Diameter (mm) | C | Si | Mn | P | S | Ni | Cr | Mo |
|---|---|---|---|---|---|---|---|---|---|
| CG | 0.8 | 0.03 | 0.44 | 1.04 | 0.031 | 0.005 | 9.03 | 18.06 | — |
| | 0.4 | 0.02 | 0.40 | 1.05 | 0.034 | 0.005 | 10.06 | 18.07 | — |
| | 0.2 | 0.018 | 0.363 | 1.086 | 0.0341 | 0.0015 | 10.052 | 18.152 | — |
| UFGSS | 0.8 | 0.06 | 0.25 | 1.66 | 0.040 | 0.026 | 8.02 | 18.72 | — |
| | 0.4 | 0.05 | 0.30 | 1.41 | 0.039 | 0.002 | 9.06 | 18.12 | — |
| | 0.2 | 0.06 | 0.25 | 1.66 | 0.040 | 0.026 | 8.02 | 18.72 | — |

The metal samples tested were type 316 stainless steel wires having different diameters (φ in mm) and different average grain sizes (in μm). Ultrafine average grain size (UGCSS) vary from 0.22 μm to 0.27 μm and conventional grain size vary from 12 μm to 21.5 μm CG304 φ0.8 grain size 21.5 μm CG304 φ0.4 grain size 12.0 μm CG304 φ0.2 grain size 15.0 μm UFGSS 304 φ0.8 grain size 0.27 μm UFGSS 304 φ0.4 grain size 0.22 μm UFGSS 304 φ0.2 grain size 0.23 μm Results:

Predictive equations and optimal grain size were calculated.

FIGS. 6A-6D show exemplary response profile obtained by plotting the colony-forming unit of the gram positive or gram-negative bacteria after cultivation with respect to the average crystal grain size of the crystal grain.

Figure 6A:
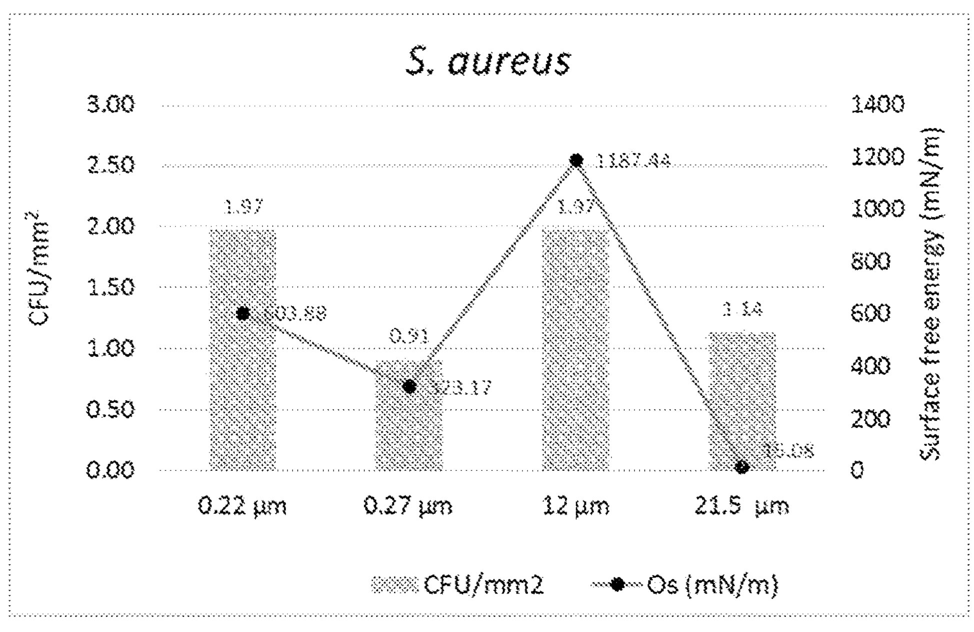
FIG. 6A is an example of a response profile obtained by plotting a response amount (CFU/ml) and surface free energy (mN/m) normalized to surface area of *S. aureus* bacteria with respect to an average crystal grain size of a crystal grain of type 304 stainless steel according to some embodiments.
Figure 6B:
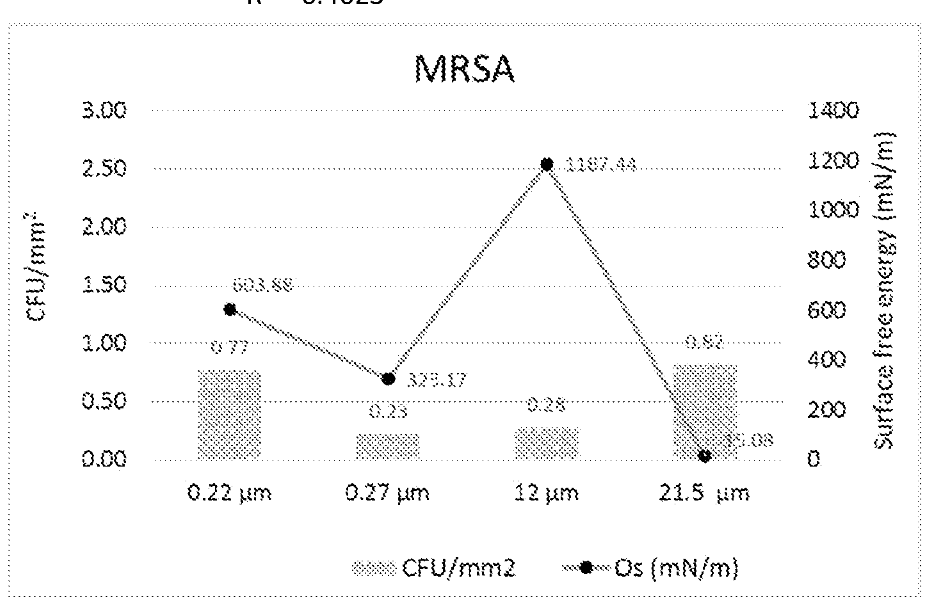
FIG. 6B is an example of a response profile obtained by plotting a response amount (CFU/ml) and surface free energy (mN/m) normalized to surface area of Methicillin-resistant *Staphylococcus aureus* bacteria with respect to an average crystal grain size of a crystal grain of type 304 stainless steel according to some embodiments.
Figure 6C:
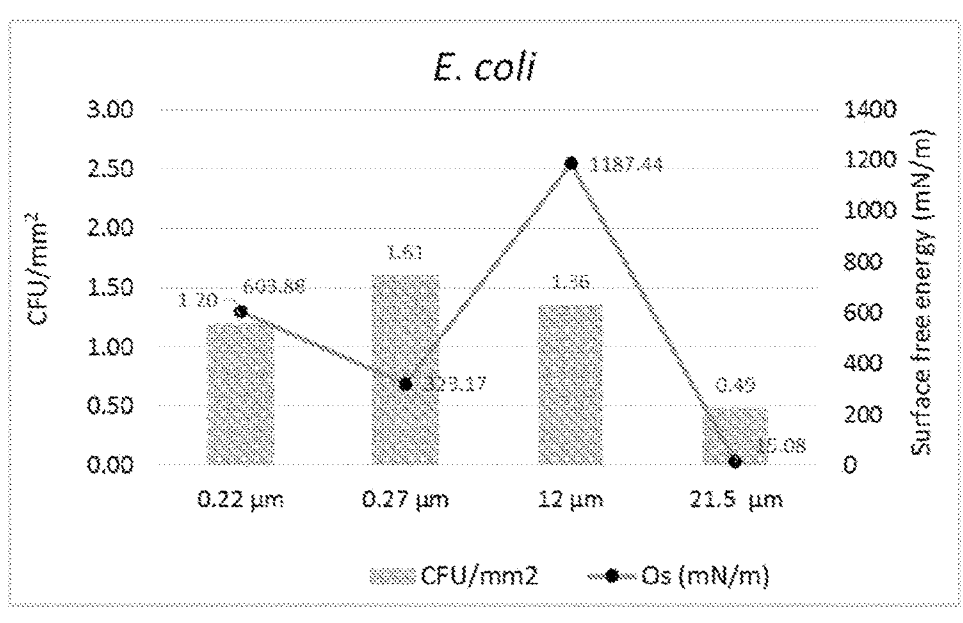
FIG. 6C is an example of a response profile obtained by plotting a response amount (CFU/ml) and surface free energy (mN/m) normalized to surface area of *E. coli* bacteria with respect to an average crystal grain size of a crystal grain of type 304 stainless steel according to some embodiments.
Figure 6D:
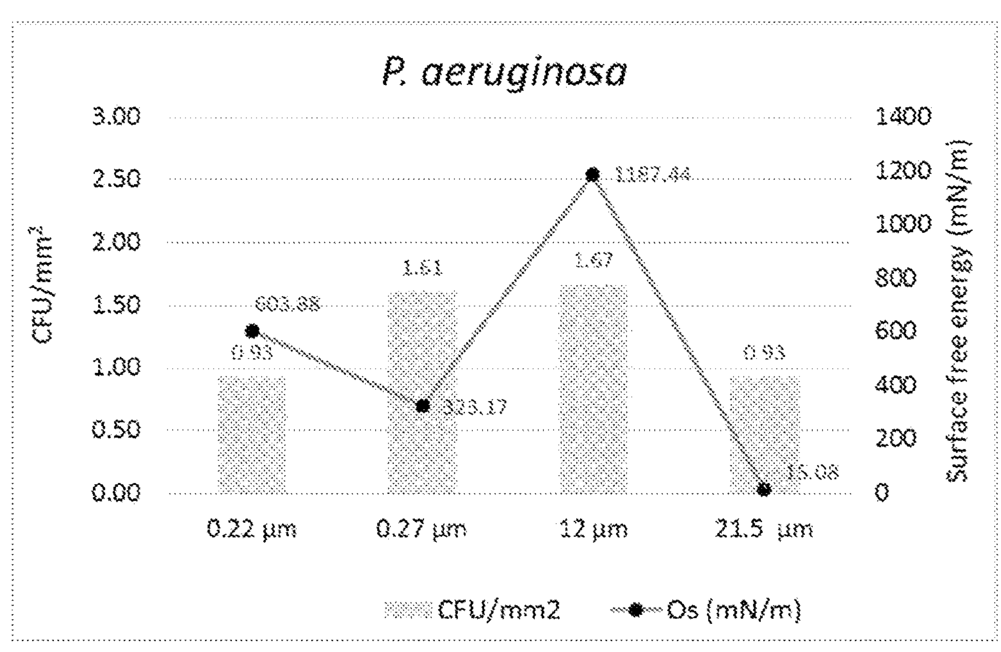
FIG. 6D is an example of a response profile obtained by plotting a response amount (CFU/ml) and surface free energy (mN/m) normalized to surface area of *P. aeruginosa* bacteria with respect to an average crystal grain size of a crystal grain of type 304 stainless steel according to some embodiments.

FIG. 6A shows the predictive equations for calculating the optimal grain size to inhibit growth/adhesion of *S. aureus* for conventional grain and ultrafine grain type 304 stainless steel metal material. FIG. 6B shows the equation for calculating the optimal grain size to inhibit growth/adhesion of MRSA for conventional grain and ultrafine grain type 304 stainless steel metal material. FIG. 6C shows the equation for calculating the optimal grain size to inhibit growth/adhesion of *E. coli* for conventional grain and ultrafine grain type 304 stainless steel metal material. FIG. 6D shows the equation for calculating the optimal grain size to inhibit growth/adhesion of *P. aeruginosa* for conventional grain and ultrafine grain type 304 stainless steel metal material.

As shown in FIGS. 6A-6D, the CFU/ml normalized to surface area for the bacteria tested ranges from 0.29 μm to 32.23 μm.

The predictive equations of FIGS. 6A, 6C-6D showed that the predicted optimal average grain size of the conventional grain size metal samples to inhibit *S. aureus, E. coli* and *P. aeruginosa* growth/absorption ranges from 27.81 μm to 32.23 μm.

The predictive equations of FIGS. 6A-6D showed that the predicted optimal average grain size of the ultrafine grain size metal samples to inhibit *S. aureus*, MRSA, *E. coli* and *P. aeruginosa* growth/absorption ranges from 0.29 and 1.59 μm.

Example 9—Effect of Grain Size Fibroblast Growth

The cytotoxicity of the metal material on Human Dermal Fibroblast (HDF) (ATCC® CCL-110™) was investigated.

Methods

First, Human Dermal Fibroblast cells were cultured in complete media (Eagle's Minimum Essential (EMEM) medium with 10% fetal bovine serum and 1% penicillin streptomycin) separately in a flask at 37° C. in a humidified incubator with 5% CO2.

Then, the cells were seeded in a 48-well plate with the metal wire samples at 5,000 cells/well in 1000 μL of cell medium, and incubated for 3, 5, and 7 days at 37° C. in a 5% CO2 humidified atmosphere.

After the incubation period of time, the culture media was removed and replaced with 1000 μL of an MTS solution at 1:5 dilution in fresh media (200 μL+1000 μL EMEM). This time, the well plate was cultivated for just 3 hours to allow for a color change. Absorbance was measured at 490 nm under an absorbance plate reader (SpectraMax). Data were expressed as percentage of cell viability.

The metal samples tested were type 316 stainless steel and type 304 stainless steel wires having different diameters and average different grain sizes as shown below:

Type 304 Stainless Steel:

CG304 φ0.8 grain size 21.5 μm
CG304 φ0.4 grain size 12.0 μm
CG304 φ0.2 grain size 15.0 μm
UFGSS 304 φ0.8 grain size 0.27 μm
UFGSS 304 φ0.4 grain size 0.22 μm
UFGSS 304 φ0.2 grain size 0.23 μm Type 316 Stainless Steel:

CG316 φ0.8 grain size 16.5 μm
CG316 φ0.4 grain size 10.7 μm
CG316 φ0.2 grain size 7.1 μm
UFGSS 316 φ0.8 grain size 0.25 μm
UFGSS 316 φ0.4 grain size 0.22 μm
UFGSS 316 φ0.2 grain size 0.18 μm The diameters and area samples of the sample tested are shown in Table 7 below:

TABLE 7

| Diameter samples (mm) | 0.2 | 0.4 | 0.8 |
|---|---|---|---|
| Area samples (mm$^2$) | 8.04 | 16.21 | 32.92 |

Figure 7A:
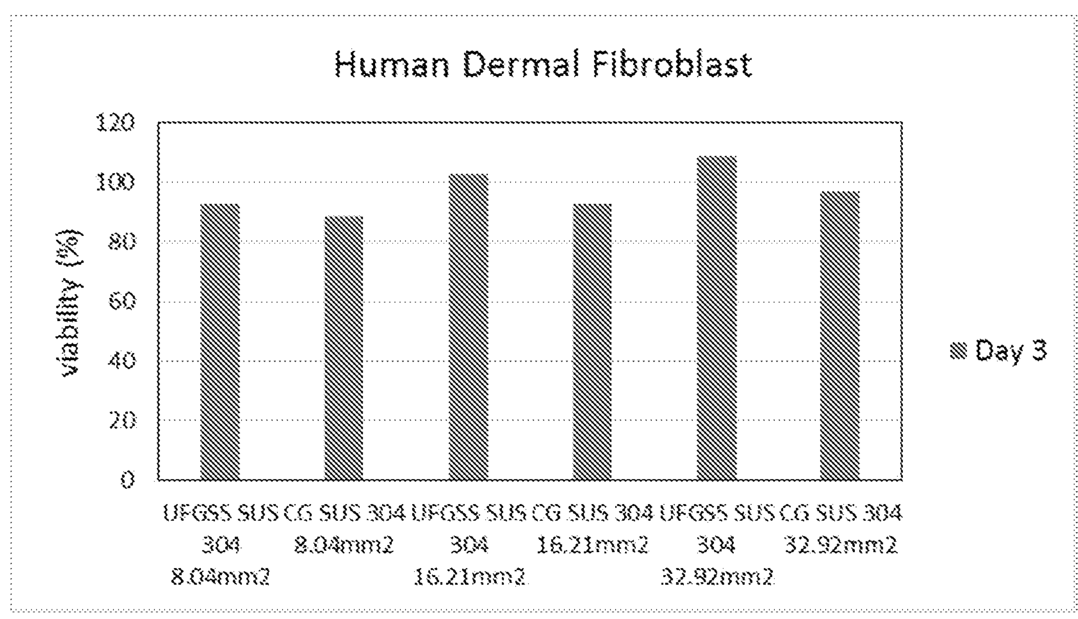
Figure 7B:
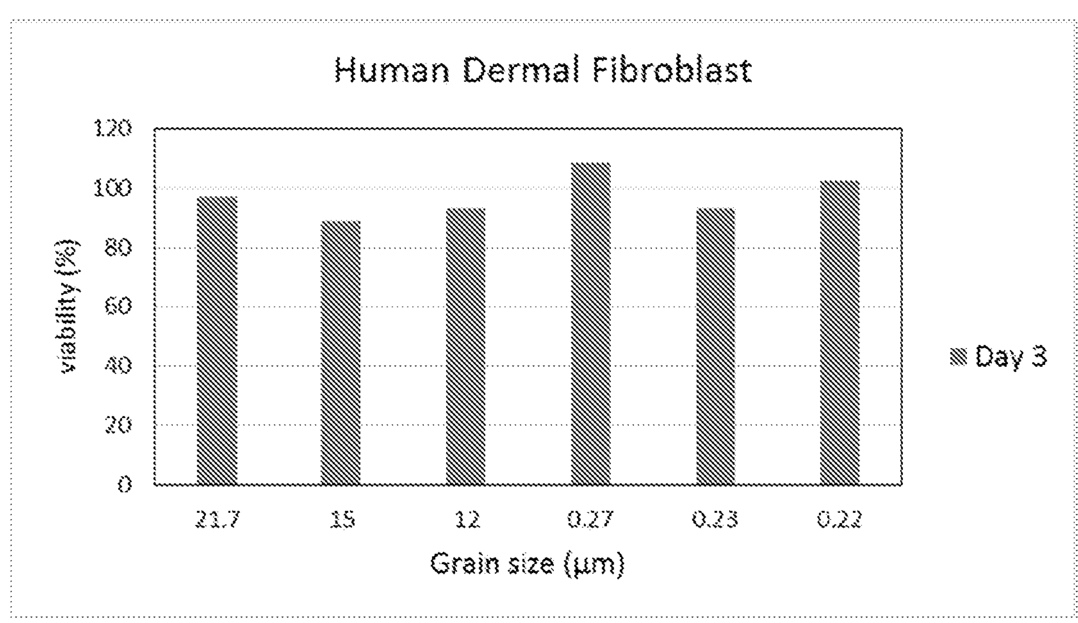

FIGS. 7A-7C show the percent viability of the human dermal fibroblast when grown on type 304 stainless steel metal samples. FIG. 7C showed that grain size of 0.22 and 0.27 μm, for conventional and ultrafine metal samples, respectively, promote human dermal fibroblasts.

Figure 8A:
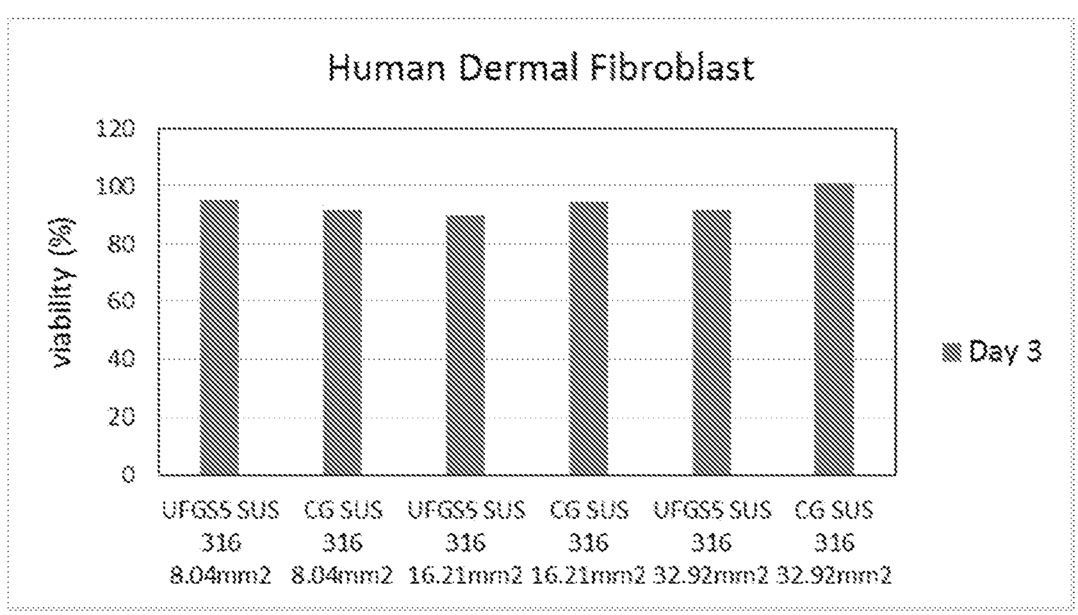
Figure 8B:
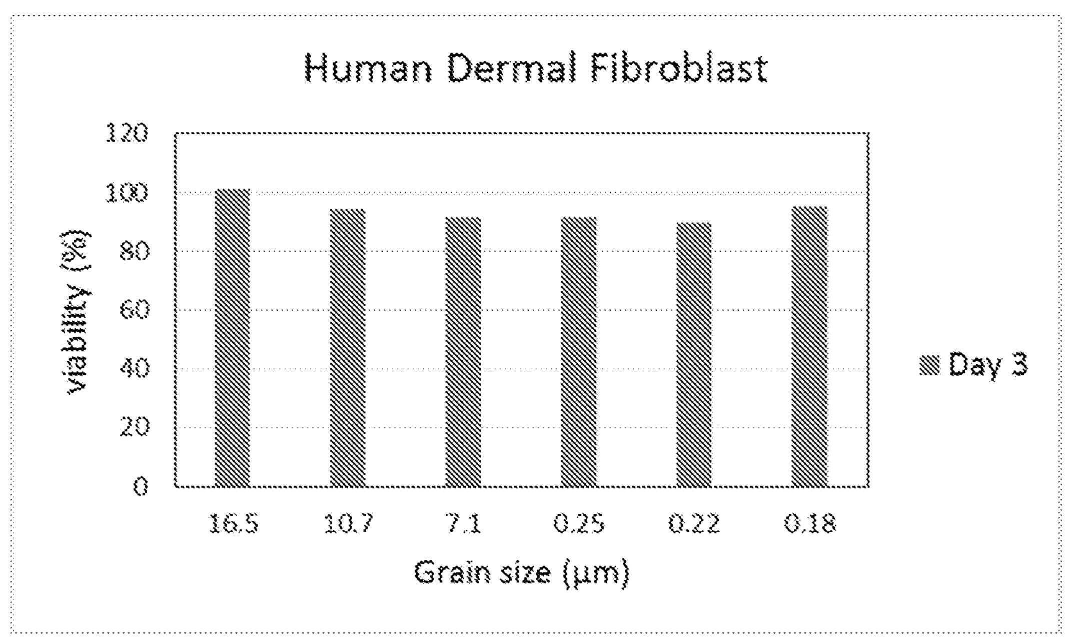

FIGS. 8A-8C show the percent viability of the human dermal fibroblast when grown on type 316 stainless steel metal samples. FIG. 8C showed that grain size of 16.5 μm, for conventional metal sample, respectively, promote human dermal fibroblasts.

Figure 9A:
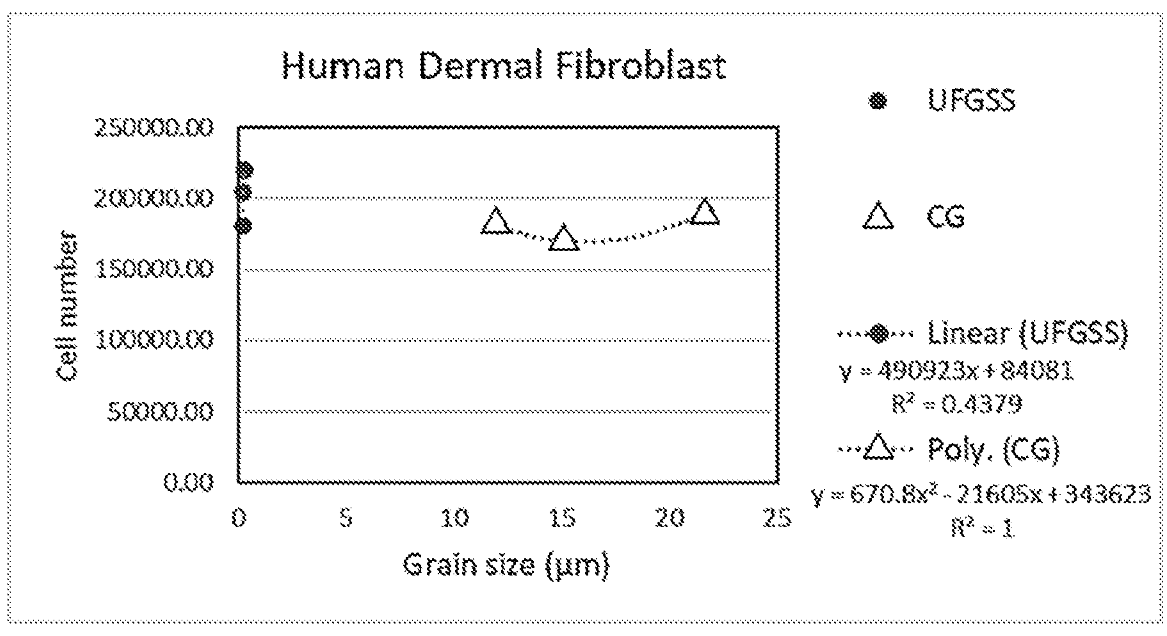
FIG. 9A is an example of a response profile obtained by plotting a response amount (cell number) normalized to surface area of human dermal fibroblasts with respect to an average crystal grain size of a crystal grain of type 304 stainless steel according to some embodiments.

The predictive equations of FIG. 9A shows that the calculated optimal grain size for type 304 stainless steel to promote human dermal fibroblast is 22.71 μm for conventional grain size metal samples and greater than 0.23 μm for ultrafine grain size metal samples.

The predictive equations of FIG. 9A shows that the calculated optimal grain size for type 304 stainless steel to promote human dermal fibroblast is 22.71 μm for conventional grain size metal samples. It should be noted that for, for example conventional grain size metal samples, the predicted grain size of 22.71 μm is similar to the range of 27.81 μm to 30.66 μm calculated as the optimal grain size to inhibit *S. aureus* and *E. coli* growth/absorption (see FIGS. 6A-6D).

Figure 9B:
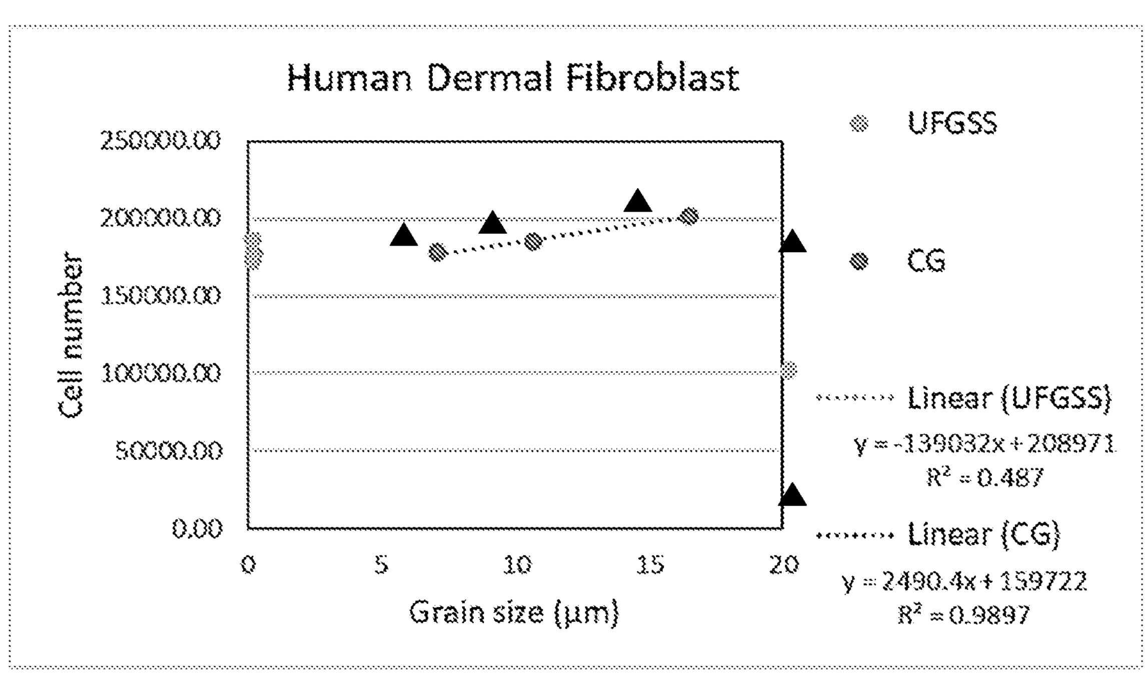
FIG. 9B is an example of a response profile obtained by plotting a response amount (cell number) normalized to surface area of human dermal fibroblasts with respect to an average crystal grain size of a crystal grain of type 316 stainless steel according to some embodiments.

The predictive equations of FIG. 9B shows that the calculated optimal grain size for type 316 stainless steel to promote human dermal fibroblast is greater than 15.88 μm for conventional grain size metal samples and greater than 0.07 μm for ultrafine grain size metal samples. It should be noted that for, for example conventional grain size metal samples, the predicted grain size of 15.88 μm falls within the range of 16.46 μm to 25.71 μm calculated as the optimal grain size to inhibit *S. aureus, E. coli* and *P. aeruginosa* growth/absorption (see FIGS. 5A-5D).

Example 10: Osteoblast Cell Growth Data Using Titanium Alloy

Human Fetal Osteoblast Cells (hFOB) (CRL-11372, ATCC) Cytotoxicity Studies

Human Fetal Osteoblast cells were cultured in complete media (Dulbecco's Modified Eagle Medium (DMEM/F12) with 10% fetal bovine serum and 1% penicillin streptomycin) separately in a flask at 37° C. in a humidified incubator with 5% CO2. Cells were then seeded in a 48-well plate with the wire samples at 5,000 cells/well in 1000 μL of cell medium, and incubated for 3, 5, and 7 days at 37° C. in a 5% CO2 humidified atmosphere. After the incubation period of time, the culture media was removed and replaced with 1000 μL of a PrestoBlue solution at 1:10 dilution in fresh media (100 μL+900 μL DEMEM/F12). This time, the well plate was cultured for 45 minutes to allow for a color change. Fluorescence was measured at 560 nm excitation wavelength and 590 nm emission wavelength under a plate reader (SpectraMax). Data were expressed as percentage of cell viability.

Table 12 show the titanium alloy samples used.

TABLE 12

| Samples (Length 12.7 mm) | Diameter (mm) | Area (mm2) |
|---|---|---|
| Grain size 8.8 μm | 1.7 | 72.37 |
| Grain size 3.1 μm | 1.7 | 72.37 |
| Grain size 2 μm | 1.7 | 72.37 |
| Grain size 1.6 μm | 1.7 | 72.37 |
| Grain size 0.8 μm | 1.7 | 72.37 |

TABLE 12-continued

| Samples (Length 12.7 mm) | Diameter (mm) | Area (mm2) |
|---|---|---|
| (*)Control sample 1: Ti6/4Eli | 1.57 | 66.73 |
| (*)Control sample 2: Ti6/4Eli | 1.98 | 85.21 |

(*)Unknown grain size

Table 13 show composition of the titanium alloy control samples

TABLE 13

| ASTM F136 Titanium | |
|---|---|
| Nitrogen, max. | 0.05 |
| Carbon, max. | 0.08 |
| Hydrogen, max. | 0.012 |
| Iron, max. | 0.25 |
| Oxygen, max. | 0.13 |
| Aluminum | 5.50-6.50 |
| Vanadium | 3.50-4.50 |
| Titanium | Balance |

Cell Growth Assays Using Human Fetal Osteoblast (hFOB) Cells.

Figure 11:
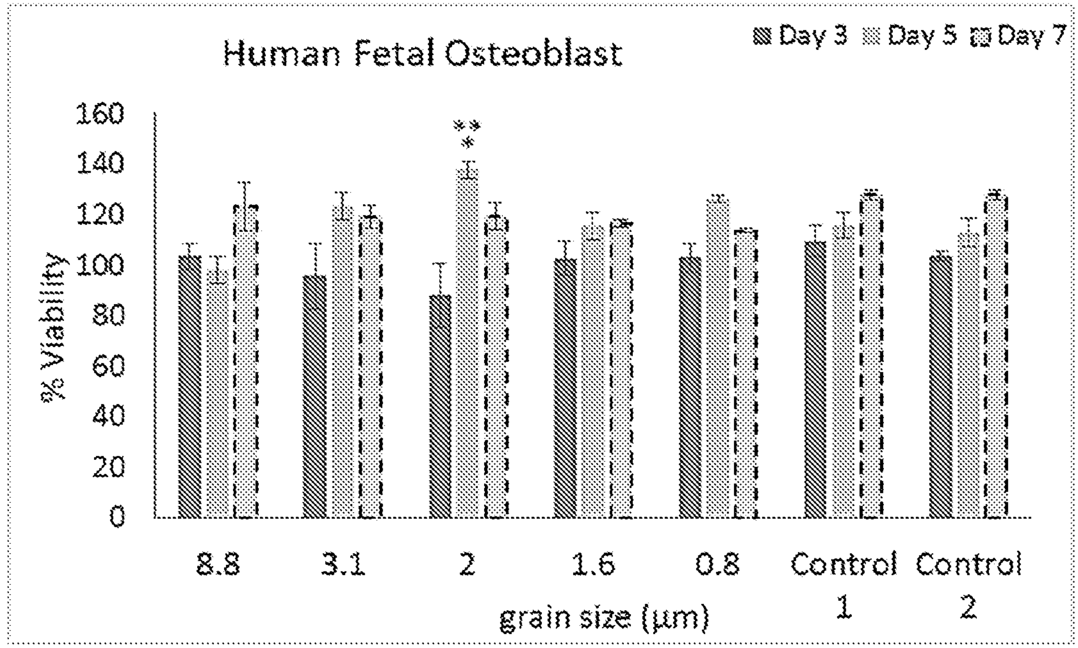
FIG. 11 is a graph showing the percent viability of Human Fetal Osteoblast in cell growth assay on titanium alloy according to some embodiments.

For all samples tested, the percentage of viability was higher than 80%, during the 7 days incubation, showing a relatively low cytotoxicity against hFOB cells (see FIG. 11).

Moreover, the percentage of viability vales was higher than 100% in most of the cases, which indicates that a higher number of cells grew in presence of the samples compared with the number of cells that grew in contact with just fresh media. Without being bound to the theory, cells grew on the top of the titanium samples, which promoted their proliferation.

The percentage of cell viability slightly decreased for samples with a grain size of 3.1, 2, and 0.8 μm after day 5.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

What is claimed is:

1. A metal material comprising a crystal grain having an average crystal grain size from 40 nm to 30 μm configured (i) to inhibit adhesion, growth or combination thereof of microorganisms, or (ii) to inhibit adhesion, growth or combination thereof of predetermined eukaryotic cells, wherein the metal material has a surface roughness, Ra, in arithmetic roughness, at the nanoscale from 1.605 nm to 2.044 nm.

2. The metal material according to claim 1, wherein the metal material is stainless steel.

3. The metal material according to claim 1, wherein the metal material has an average crystal grain size for substantially inhibiting adsorption or growth of the microorganism which is determined from a response profile which is a result obtained by cultivating the microorganism on a metal material having crystal grains with different average crystal grain sizes and plotting a number of the microorganism after the cultivation with respect to the average crystal grain size.

4. The metal material according to claim 1, wherein the crystal grain has an average crystal grain size from 200 nm or more to 10 μm or less.

5. The metal material according to claim 1, wherein the crystal grain has an average crystal grain size from 1 μm or more to 10 μm or less.

6. The metal material according to claim 2, wherein the metal is type 316 stainless steel.

7. The metal material according to claim 1, wherein the microorganism is a gram+bacterium.

8. The metal material according to claim 1, wherein the microorganism is a gram−bacterium.

9. The metal material according to claim 1, wherein the microorganism is one of *Staphylococcus aureus, Staphylococcus epidermidis*, Methicillin-resistant *Staphylococcus aureus* (MRSA), *E. coli, Pseudomonas aeruginosa.*

10. A wire or a rod made from the material according to claim 1.

11. The wire or rod wherein of claim 10, wherein the average crystal grain size is from 200 nm or more to 10 μm or less.

12. A medical device made from the material according to claim 1.

13. A foil made from the material according to claim 1.

14. An instrument made from the material according to claim 1.

* * * * *